United States Patent [19]

Lachmann et al.

[11] Patent Number: 5,752,509
[45] Date of Patent: May 19, 1998

[54] ARTIFICIAL VENTILATION SYSTEM

[75] Inventors: Burkhard Lachmann, Lindenstr. 47a, D-26123 Oldenburg, Germany; Govinda Rajan, Rochelle Park, N.J.; Stephan Böhm, Bergisch Gladbach, Germany

[73] Assignee: Burkhard Lachmann, Oldenburg, Germany

[21] Appl. No.: 679,369

[22] Filed: Jul. 10, 1996

[30] Foreign Application Priority Data

Jul. 10, 1995 [SE] Sweden ................................ 9502543

[51] Int. Cl.$^6$ ................................ A61M 16/00
[52] U.S. Cl. ................ 128/204.23; 128/204.21; 128/203.12; 128/203.14
[58] Field of Search .............. 128/204.23, 204.21, 128/203.12, 205.12, 205.11, 204.18, 911, 912, 719, 671, 728, 203.14, 204.26

[56] References Cited

U.S. PATENT DOCUMENTS

| | | | |
|---|---|---|---|
| 3,734,091 | 5/1973 | Taflin | 128/204.23 |
| 4,211,221 | 7/1980 | Schwanbom | 128/204.26 |
| 4,326,513 | 4/1982 | Schulz et al. | 128/203.14 |
| 4,889,116 | 12/1989 | Taube | 128/204.23 |
| 4,917,080 | 4/1990 | Bayeflein | 128/204.23 |
| 4,986,268 | 1/1991 | Tehrani | 128/204.21 |
| 5,020,516 | 6/1991 | Biondi et al. | 128/671 |
| 5,103,814 | 4/1992 | Maher | 128/204.18 |
| 5,365,922 | 11/1994 | Raemer | 128/204.23 |
| 5,388,575 | 2/1995 | Taube | 128/204.23 |
| 5,437,272 | 8/1995 | Fuhraram | 128/203.12 |
| 5,575,283 | 11/1996 | Sjoestrand | 128/204.23 |

FOREIGN PATENT DOCUMENTS

| | | | |
|---|---|---|---|
| 0 504 725 | 9/1992 | European Pat. Off. | A61B 5/083 |
| 501 560 | 3/1995 | Sweden | A61M 16/00 |

OTHER PUBLICATIONS

"Open up the lung and keep the lung open," Lachmann, Intensive Care Med (1992) vol. 18, pp. 319–321.
"An Adaptive Lung Ventilation Controller," IEEE Trans. On Biomed. Eng., vol. 41, No. 1, Jan., 1994, pp. 51–59.
"Automatic Weaning From Mechanical Ventilation Using An Adaptive Lung Ventilation Controller," Linton et al., Chest., Dec. 1994, vol. 106(6), pp. 1843–1850.

*Primary Examiner*—Vincent Millin
*Assistant Examiner*—V. Seurastava
*Attorney, Agent, or Firm*—Hill & Simpson

[57] ABSTRACT

In an artificial ventilation system and a method for controlling the artificial ventilation system for obtaining an optimized artificial ventilation of a lung system of a patient, optimal artificial ventilation is obtained when the blood system of the patient is maximally oxygenated and, at the same time, the negative influence on the cardio-pulmonary system is minimized. The ventilation system has a gas delivery unit for delivering controllable inspiration pulses to a patient, a monitoring unit for measuring at least one parameter related to the function of the lung system, such as a blood gas analyser, and a control unit for determining an optimal peak inspiratory pressure and pressure amplitude for the inspiration pulse based on the measured blood gas parameter.

27 Claims, 12 Drawing Sheets

ARTIFICIAL VENTILATION SYSTEM

BACKGROUND OF THE INVENTION

1. Field of the Invention

The present invention relates to an artificial ventilation system of the type having a respiratory gas delivery unit, connectable to a lung system for delivering controllable inspiration pulses of respiratory gas to the lung system, a regulating unit operatively connected to the respiratory gas delivery unit for controlling the inspiration pulses based on a control signal supplied to the regulating unit, a monitoring unit for measuring at least one parameter related to the function of the lung system, and a control unit connected to the monitoring unit for determining a change in an inspiration pulse parameter.

The present invention also relates to a method for controlling an artificial ventilation system.

2. Description of the Prior Art

As used herein, the term inspiration pulse includes all relevant parameters which in any way define the inspiration pulse itself and its effect on a lung system. For example, the positive end expiratory pressure (PEEP) is normally set as an external overpressure on the lungs at the end of each expiration. The following inspiration pulse, however, will commence at this elevated pressure and the effect of the inspiration pulse on the lungs is also dependent on PEEP. PEEP is therefore also a relevant parameter for the inspiration pulse. The same reasoning is valid when regarding expiration time, since the effect of a particular inspiration pulse is also dependent on, inter alia, the ratio between inspiration time and expiration time.

The lungs are one of the most important organs in a living being. The main function of the lungs is the gas exchange between the organism and the environment. Oxygen ($O_2$) in the air is diffused into the blood system and carbon dioxide ($CO_2$) diffuses from the blood system to the air in the lungs. The $CO_2$ is then removed from the lungs during expiration. The actual exchange of gas takes place in the air/fluid interface in the alveoli. There are about 300 million alveoli in a healthy human lung system, having a total area of about 100 m$^2$. The alveoli are enmeshed in the pulmonary capillary network, which forms a fine network of minute capillaries. The capillaries are so thin that only one red blood cell at a time can pass through.

As a result of injuries or disease or even due to artificial ventilation (such as during anaesthesia), the function of the lung can be effected to such a degree that the patient (normally a human being or a domestic animal) cannot maintain a sufficient spontaneous respiration. Artificial respiration, or ventilation, must then be provided. The simplest and fastest way of providing artificial respiration in acute situations is mouth-to-mouth respiration. This is, however, not sufficient for prolonged treatment, nor for all kinds of acute illnesses.

Mechanical artificial respiration has been known for a long time, for instance by the so called iron lung. The iron lung comprises a chamber which covers the patient up to the neck. To force the patient to inhale, air is pumped out of the chamber, thereby forcing the chest to expand. Air will then flow down into the lungs. The bulky chamber and the problem of having the patient's body completely encased, are major disadvantages for this kind of artificial respiration, which usually is referred to as negative pressure respiration.

During the polio epidemic in the 1950's a large number of patients were suddenly in great need for artificial respiration. Positive pressure respiration was then developed. In principal a piston pump was used for creating an overpressure which, via a tube and a breathing mask, forced air into the patient's lungs. The pumps were at the beginning manually controlled, normally by students, who regularly pumped air into the patients lungs. Mechanical driving mechanisms for the pump were then developed.

Most of these first positive pressure ventilation systems controlled the tidal volume ($V_t$) of the patient, as they forced a defined volume, i.e. the pump's stroke volume, into the patient's lungs during each inspiration. As long as the lungs have a good compliance, this causes no problem. But when there are atelectatic regions, i.e. the lung is "stiff", the supplied volume can cause pressures within the lungs which harm the lung. The pressure difference between different regions of the lung may give rise to shear forces, which damage the lungs and prolong the recovery of the patient. A high absolute pressure may cause neighboring alveoli to compress an interjacent capillary and prevent the vital blood flow (overdistension). In severe cases, excessive pressure may even cause tissue rupture.

Since then, artificial ventilation systems have been greatly improved. In the 60's, electronically controlled ventilators were developed, which could control pressure and flows with higher accuracy than the preceding mechanic ventilators. Several new ventilation modes were developed as well.

In a modern state of the art ventilator system, such as the Servo Ventilator 300, Siemens-Elema AB, Sweden, the physician may select among a vast number of ventilation modes, such as pressure control (PC), pressure support (PS), volume control (VC), volume support (VS), pressure regulated volume control (PRVC), continuous positive airway pressure (CPAP), synchronized intermittent mandatory ventilation (SIMV), and others, including variations of these modes. It is also possible to use one and the same ventilator for neonatal, paediatric and adult patients.

Providing only respiratory air to a patient's lungs, however, is not sufficient. Since all lung systems are individual and may for instance display different compliance and more or less atelectatic regions, any treatment must be adapted to the specific patient. In particular, when using positive pressure ventilation, care must be taken not to supply too high pressures or volumes of respiratory gas; since these can cause barotrauma and volutrauma. As already mentioned, overdistension and even tissue rupture within the lungs may be caused by extreme peak pressures. Another risks is depletion of surfactant in the alveoli, due to large tidal volumes ($V_t$) and pressure changes, end expiratory lung volume less than the lung's functional residual capacity (FRC), as well as repeated transgressions from closed to open state. The depletion of surfactant causes the lung to stiffen. As the patient's condition changes (improves or deteriorates), the treatment must also change. Another mode could be selected or a change could be made in one of the numerous parameters related to the inspiration pulse. The importance of monitoring the condition of the patient was therefore realised at an early stage and this area has also been developed.

Lung mechanics were probably the first factor to be considered by physicians when determining how to treat a certain patient. By using spirometers combined with other instruments some lung mechanic parameters, such as tidal volume, residual volume and functional residual capacity (FRC), could be determined. Resistance and compliance have also been determined for lungs, by different measurement and calculation methods. These parameters could be used by the physician to determine the condition of the lungs. Another factor which had to be taken into consideration was the dead space. For the normal lung system the mouth, nose, pharynx, trachea and bronchi comprise the anatomic dead space. In addition to this, the tubing connecting the ventilation system to the patient adds to the dead space, thereby increasing rebreathing of exhaled $CO_2$-enriched gas. Thus, the $CO_2$ also had to be considered in order to improve ventilation of the lung system and, in particular to avoid hypoventilation (resulting in a too high blood $CO_2$ level) and hyperventilation (resulting in a too low blood $CO_2$ level).

Apart from these additional considerations, general monitoring of the condition of the patient has become an important tool, especially in intensive care. Normally, monitoring can include measurement of ECG, EEG, $CO_2$, oxygen saturation is ($S_aO_2$) and, more recently, partial pressure of oxygen ($P_aO_2$) and carbon dioxide ($P_aCO_2$) in the blood. The experienced physician will then try to ventilate the patient in order to obtain certain life supporting values of these monitored parameters, such as a sufficient oxygen saturation.

For some inspiration pulse parameters, closed loop systems have been described, where a measured body function parameter is utilized in a control system for automatically changing the inspiration pulse parameter. In a ventilator system described in U.S. Pat. No. 5,103,814, the measured $S_aO_2$ of the patient is used for controlling the percentage of oxygen in a respiratory gas. In other words, if the $S_aO_2$ is below a threshold value, a higher percentage of oxygen ($F_iO$) will be supplied to the patient and if the $S_aO_2$ is higher than the threshold value, the $F_iO$ in the respiratory gas will be reduced. A similar system is described in European Application 504 725. One major problem for these systems is: changing one parameter is not sufficient. For instance, if the lungs suddenly collapse, even an increase to 100% $O_2$ is not sufficient have an optimal gas exchange.

Other attempts at automation have also been made. In an article entitled "Automatic weaning from mechanical ventilation using an adaptive lung ventilation controller", Linton et. al., Chest 1994 Dec.; 106 (6): 1843–1850, a system for automatic weaning of a patient is described. The described system was automatically adapted to the lung mechanics of the patient on a breath to breath basis and aimed to minimize work of breathing, to maintain alveolar ventilation and to prevent intrinsic PEEP. In U.S. Pat. No. 4,986,268 a more complete control is sought. Oxygen and carbon dioxide contents in expired air are measured and based on these, together with predetermined lung elastance and air viscosity factors, the tidal volume (Vt) and respiratory rate (RR) are automatically calculated and set. Yet another system is described in an article entitled "An adaptive lung ventilation controller", by Laubscher et. al., IEEE Trans. Biomed. Eng. 1994 Jan; 41(1):51–59. In this system the physician programs a desired gross alveolar ventilation and the control system tries to maintain this desired level by automatically adjusting the mechanical rate and inspiratory pressure level. The adjustments are based on measurements of the patient's lung mechanics and series dead space.

Although these systems may provide automated system solutions for certain functions, or a certain category of patients, they do not succeed in presenting full automatic control of a patient's breathing, irrespective of the condition of the patient and most do not aim at accelerating the recovery time.

In summary, are many parameters and factors to consider when deciding how to apply the best possible artificial ventilation on a specific patient. Many parameters relating to the condition of the patient and/or the lung system have been found, but the interrelation between the parameters and how they should be utilized for optimum treatment has not been resolved. Problems which can arise are insufficient oxygenation, hypoventilation, hyperventilation, volutrauma, barotrauma, overdistension, tissue rupture, shear forces, etc. In particular, although it has always been the purpose of obtaining an optimal artificial ventilation for a patient, such a system has never been realized.

SUMMARY OF THE INVENTION

It is an object of the invention to achieve an artificial ventilation system which obtains an optimal artificial ventilation for a patient, considering the most relevant parameters for the condition of the patient and aiming at an improved recovery time for the patient and the lung system.

It is also an object of the invention to achieve a method for controlling an artificial ventilation system in such way.

Basically, it has now been recognized that the vital importance of artificial ventilation is to reduce the pressure load on the lung system and at the same time achieve a sufficient oxygenation of the blood system. This will provide a life sustaining condition, with a minimum of negative effects for the patient.

In principle, the basic characteristics of the alveoli have to be taken into account. The alveoli can be described with reference to the LaPlace law, i.e. $P=2\gamma/r$, where P is a pressure required to sustain a particular radius of a bubble, $\gamma$ is the surface tension of the fluid gas interface and r is the radius of the bubble. A collapsed alveolus requires a relatively high pressure in order to begin to inflate, but as the radius increases when the alveolus expands, the pressure required for further inflation is reduced. In other words, when the alveoli are inflated, they will not require a high pressure to remain open. The importance of maintaining the lung open is described in more detail in an article entitled "Open up the lung and keep the lung open", Intensive Care Medicine, 1992, 18:319–321. The artificial ventilation system of the present invention takes advantage of this characteristic, extrapolated onto the whole lung, and combines it with a vital life supporting parameter, the oxygenation of the blood system.

By minimizing the pressures supplied to the lung, in particular peak pressure and pressure amplitude, the negative effects of the cardiopulmonary system, such as barotrauma, volutrauma, overdistension and hypoxic vasoconstriction can be minimized, if not completely avoided. The artificial ventilation system operates most efficiently in the pressure control mode, when the patient does not breathe spontaneously, and in support modes, when the patient breathes spontaneously. Other modes of operation, however, can be used with the same advantageous results. For instance, in volume control mode the pressure could be measured and the supply of respiratory gas could be controlled so that the desired pressure parameters are obtained and maintained.

The blood gas parameter which is preferably utilized in the inventive method and apparatus is the partial pressure of oxygen ($P_aO_2$). $P_aO_2$ is the best blood gas parameter, which reflects the oxygenation of the blood system. $P_aO_2$ is better than, for instance, saturation of oxygen in blood ($S_aO_2$) or by calculating arterial oxygenation by measuring expired oxygen content. This because $P_aO_2$ varies even when the blood is fully saturated.

The system can operate completely automatically, since all relevant parameters can be measured automatically on site. As will be described below, other operations are also possible.

The invention also relates to a method for controlling the artificial ventilation system in order to obtain the optimum ventilation.

In one embodiment of the invention, the expiration flow is measured in a flow meter and optimal settings for inspiration/expiration time ratio (I:E ratio) and respiration rate (RR) are determined based on the quotient between a determined end expiratory flow ($\phi_{EE}$) and a peak expiratory flow ($\phi_{PE}$).

In another embodiment of the invention, a monitor screen is connected to the monitoring unit for displaying measured parameters. The monitor screen could also be connected to the control unit for displaying determined inspiration pulse parameters. Using a monitor screen provides a perfect interface between the artificial ventilation system and a physician. The physician can select whether the artificial ventilation system should operate automatically and control the entire ventilation of the patient itself, or if the control unit should only display the suggested new parameters on the screen, whereupon the physician decides whether or not to use the suggested parameters for the treatment or diagnosis of the patient. The monitor screen and monitoring unit may be parts of a total monitoring system for the patient. For instance, in intensive care, monitoring of ECG, EEG, haemodynamic parameters, such as blood pressures, oxygen saturation, partial pressure of oxygen and carbon dioxide in the blood, oxygen consumption, carbon dioxide production and other parameters can be measured and displayed on the monitor screen.

In all, this provides a ventilation system which has a great potential for all artificial ventilation. In hospitals, the ventilator system may even be utilized as an education tool for the staff. The interface operation via the monitor screen presents at all stages information of the patients condition and how to ventilate the patient in each instance.

In a further embodiment of the invention the condition of the lungs is first determined by checking whether the lungs are collapsed or not. This is reflected in the partial pressure of oxygen in the blood. If the lungs are collapsed, an opening pressure procedure will be activated. When an opening pressure ($P_o$) has been determined, a closing pressure ($P_c$) of the lung system will also be determined. The closing pressure ($P_c$) will then reflect the lowest pressure, at which the lungs may be ventilated to provide for a sufficient oxygenation of the blood.

The inventive method for controlling the artificial ventilation system preferably employs a number of logical rules, or protocols. By evaluating the condition of the lungs at pre-determined intervals, a defined set of rules, or a particular protocol, can be activated when necessary. In particular, the present invention includes an opening protocol, a reduction protocol, a maintenance protocol and a weaning protocol. The opening protocol provides for the determination of the opening pressure ($P_o$). The reduction protocol provides for the determining of the closing pressure ($P_c$). The maintenance protocol aims to keep the lungs open. The weaning protocol, finally, is activated when the patient has improved enough to be weaned from the artificial ventilation. Since these protocols follow the condition of the patient, they will normally always follow in the same consecutive order: opening protocol, reduction protocol, maintenance protocol and weaning protocol.

DESCRIPTION OF THE PREFERRED EMBODIMENTS

Figure 1:
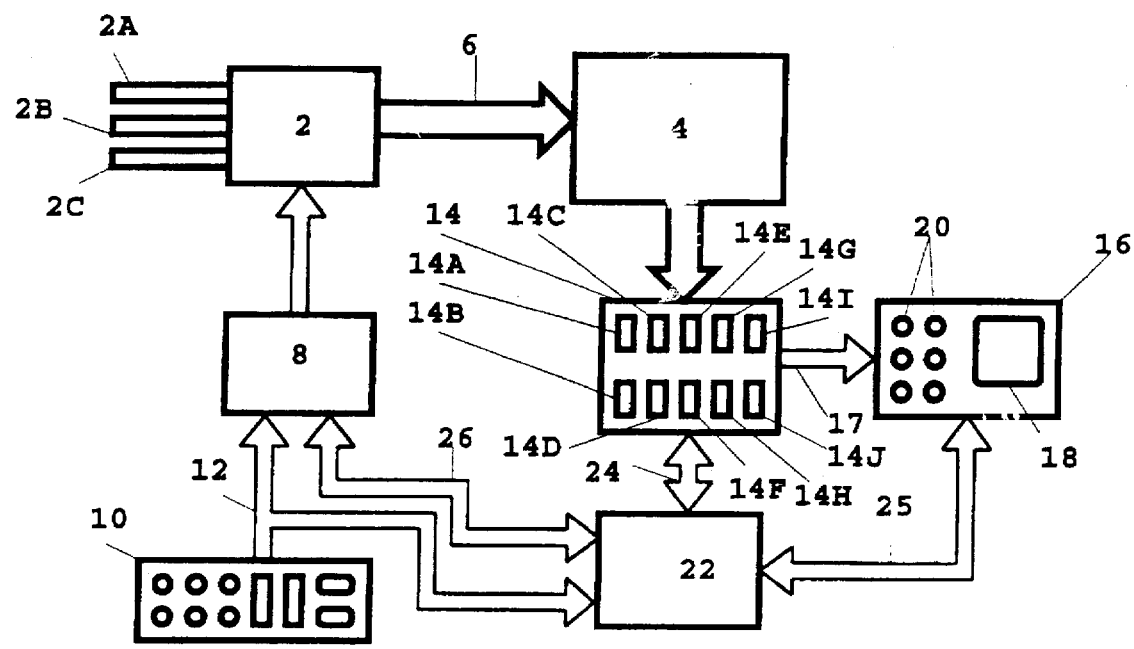
FIG. 1 is a schematic illustration of an embodiment of an artificial ventilation system constructed and operating in accordance with the principles of the present invention.

As shown in FIG. 1, the artificial ventilation system of the invention has a gas delivery unit 2, which receives controllable amounts of gas via gas inlets 2A, 2B, 2C. The received gases are mixed in predetermined fractions within the gas delivery unit 2 and are then delivered to the lung system of a patient 4, via a gas delivery system 6. Respiratory gas can be delivered intermittently, during inspiration phases or constantly, whereby an inspiration pulse of respiratory gas is superimposed during the inspiratory phase. The gas delivery unit 2 is regulated by a regulating unit 8, which regulates the flow, pressure, gas mix, timing, etc. of the respiratory gas. All these inspiration pulse parameters can be entered on a control panel 10 by a physician or other clinical staff, whereby a control signal is transferred from the control panel 10 to the regulating unit 8 via a databus 12. The control panel 10 can also be equipped with the possibility of entering patient information such as age, sex and body weight or size, which may be used for further optimization of the treatment. Other possible information which can be entered to have an impact on the system are, the reason for the artificial respiration (illness, insufficient respiration, insufficient respiratory muscles etc.), and information regarding the physical condition of the patient (cyanosis, chest wall movements, emphysema, skin temperature, etc.).

The patient 4 is also connected to a monitoring unit 14. The monitoring unit 14 includes a blood gas analyser 14A, which is connected to the blood system of the patient 4, a flow meter 14B for measuring respiratory gas flow to and from the 35 lung system of the patient 4, a pressure gauge 14C for measuring the pressure in or near the lung system of the patient 4, a blood pressure meter 14D for measuring the blood pressure of the blood system of the patient 4 and a $CO_2$-meter 14E for measuring the carbon dioxide content in the expired respiratory gas.

Other components of the monitoring unit 14 can be an oxygen meter 14G, a lung mechanics meter 14H, an electrocardiograph 14I and an electroencephalograph 14J. Meters for body temperature and other parameters reflecting the patient's condition can also be included in the monitoring unit 14.

All measured parameters can be transferred to a monitor screen 16 via a databus 17. In the monitor screen 16, graphs or values can be displayed on a display 18. A physician can select which parameters to view via control knobs 20. The monitor screen 16 may also be equipped with the capability of entering patient data, as described above for the control panel 10. The monitoring unit 14 is also connected to a control unit 22 via a databus 24. The control unit 22 is further connected to the control panel 10 via the databus 12 and receives from the control panel 10 the set inspiration pulse parameters, as well as the selected ventilation mode and the type of patient, i.e. whether the patient is neonatal, paediatric or adult. It can, thus, also receive information about the patient's weight or size, age and sex, all entered on the control panel 10 or on the monitor screen 16. On the basis of the measured parameters from the monitoring unit 14 and the current settings on the control panel 10 and monitor screen 16, the control unit 22 will calculate and determine an optimal new setting for the artificial ventilation system and in particular an optimal setting for the inspiration pulse, such as peak inspiratory pressure (PIP), end pressure, positive (PEEP) or negative (NEEP), respiration rate (RR) and inspiration/expiration time ratio(I:E ratio).

The control unit 22 can also calculate parameters related to the measured parameters in the monitoring unit 14 and these calculated parameters can also be displayed on the monitor screen 16. Calculated parameters are, for instance, tidal volume, minute volume, oxygen consumption, $CO_2$ tidal production and $CO_2$ minute production. These calculated parameters can also be utilized for calculation of new settings. The change in certain parameters over time, such as blood gases, oxygen consumption, etc., can also be determined by the control unit 22 and utilized for determining new settings.

It should be noted that the blocks in FIG. 1 refer to function more than physical construction. In other words, some of the meters in the monitoring unit 14 (e.g. the flow meter 14B and the pressure gauge 14C), as well as the regulating unit 8, may be integrated with the gas delivery unit 2, whereas other meters in the monitoring unit 14, such as the blood gas analyser 14A, can consist of a separate apparatus. Likewise, the control unit 22 and the monitor screen 16 can be integrated parts of a computer, such as a PC.

The determination of new settings can be based on an iterative method, where settings are altered one at a time and the outcome of the change is monitored via the monitoring unit 14 before further changes in the settings are made. The determining can also be based on a pure mathematical calculation based on current patient data and patient data collected in a database for providing a knowledge background for the control unit 22. The database comprising the knowledge background is very useful when deciding maximum values and threshold values for both the measured parameters and the set inspiration pulse parameters.

The determined new settings can be displayed on the monitor screen 16. The displayed setting can then be regarded as a suggestion of a new setting and the physician may choose to change the setting accordingly or not. The display may also include information as to the next automatic setting for the ventilation system. In this case, the control unit 22 generates a further control signal, which is transferred to the regulating unit 8 via a databus 26. The further control signal will in this case override the control signal from the control panel 10. Preferably the physician may select whether the system should be completely automatic (closed loop ventilation), semiautomatic or manual.

Figure 2:
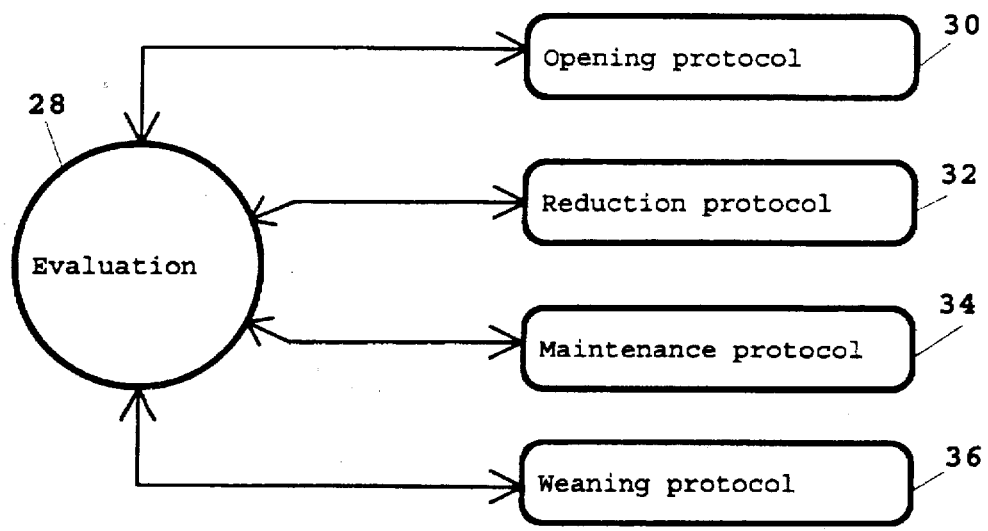
FIG. 2 illustrates the basic concept for optimizing ventilation of a lung system as used in the method and apparatus of the invention.

In order to be able to determine an optimal setting, the control unit 22 employs a set of determining protocols or control methods. In FIG. 2 a basic set of such protocols is illustrated. As the patient is connected to the ventilation system an evaluation (28) of the patient's condition is made and depending on the status of the condition, different protocols are activated by the control unit 22. Therefore, if the lung system of the patient 4 has collapsed, an opening protocol 30 will be activated, which opening protocol 30 will be described in greater detail below. If the lungs are sufficiently open a reduction protocol 32 is activated, which reduction protocol 32 is also described in further detail below. The reduction protocol 32 is mainly aimed at finding the lowest peak pressure PIP and pressure amplitude, at which the lungs remain sufficiently open. Next, a maintenance protocol 34 will be activated to keep the lung open at lowest possible pressure, but with maintained sufficient oxygenation of the blood. Finally, if the patient basically is healthy but, due to the artificial ventilation of the lung system, the respiratory muscles has become weaker or the patient has become used to the artificial ventilation, a weaning protocol 36 is activated, which also will be described in greater detail below. Normally, these protocols always follows in the same sequence: opening, reduction, maintenance and weaning.

Figure 3:
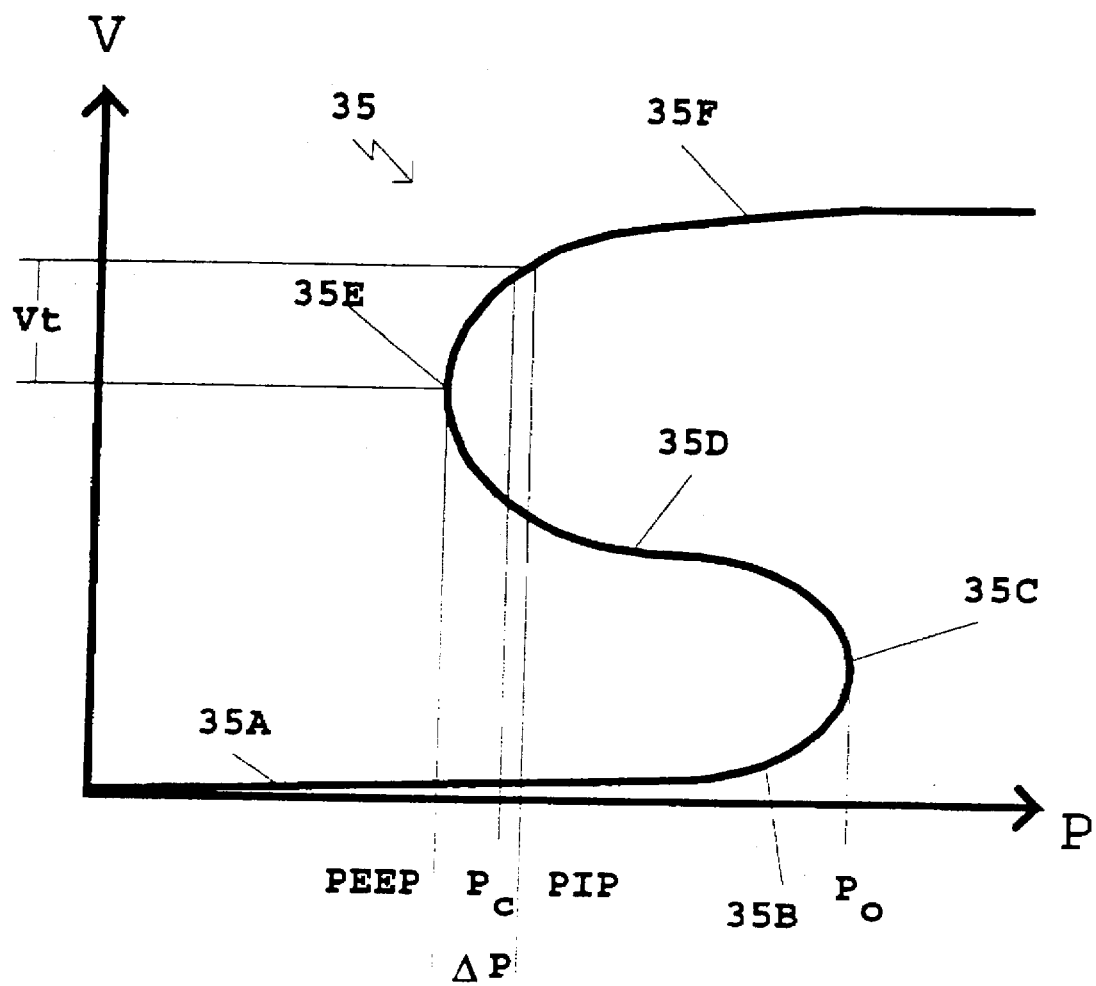
FIG. 3 shows a pressure v. volume diagram illustrating the behavior of a collapsed lung.

The present artificial ventilation system is based on the concept of providing sufficient oxygenation of the blood system with a minimum of negative effects on the cardiopulmonary system. In order to achieve this, the basic function of the lungs, and in particular the alveoli, must be considered. In FIG. 3 this is illustrated in a volume pressure diagram. In the diagram a curve 35 is drawn to illustrate the relation between volume and pressure in a collapsed alveolus. In a first region 35A of the curve 35, the pressure will increase rapidly whereas the volume only increases slowly. The reason for this was explained above, relating to the LaPlace law. A high pressure is required in order to open up the alveolus. As the alveolus begin to inflate, the volume increases (second region 35B) more rapidly. At one point 35C, the curve 35 turns. This point is referred to as the opening pressure $P_{oa}$ Of the alveolus. The alveolus will then expand, thereby causing an increase in volume at lower distension pressures. This continues all through a third region 35D, until an equilibrium is reached. At this equilibrium is a second turning point 35E. Further expansion of the alveolus will, due to the retroactive force of the tissue, require an increase in pressure. This relationship is maintained up to a fourth region 35F. Here the alveolus is so inflated that the chest physically hinders further expansion. Any increase in pressure at this stage can cause lung tissue damage and depression of the cardiovascular system. In the diagram the closing pressure $P_c$ and ideal peak inspiratory pressure PIP and positive end expiratory pressure PEEP have been indicated. The difference between PIP and PEEP is the pressure amplitude ΔP for the inspiration pulse. This relation is then extrapolated on the whole lung.

Figure 4:
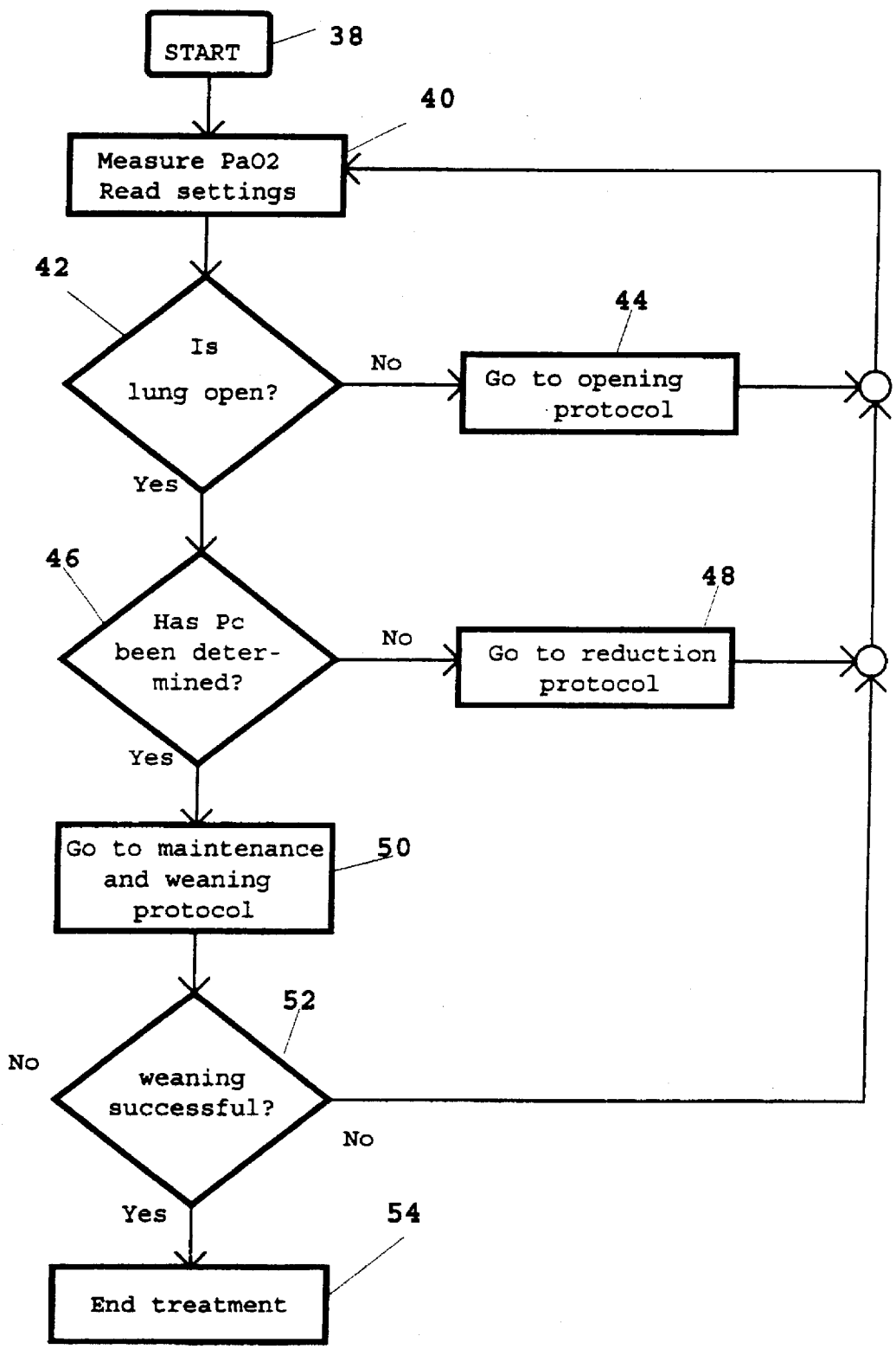
FIG. 4 is a first flow chart showing a first embodiment of a method for controlling the ventilator system of FIG. 1, in accordance with the invention.

A first method for realizing the logical sets of rules, or protocols, is shown in FIG. 4. The depicted flow chart illustrates the different steps which have to be taken, in order to obtain the optimal oxygenation. First, some further principles behind the optimum artificial ventilation of a patient will be explained, in addition to those explained in connection with FIG. 3. The idea is to provide sufficient alveolar ventilation, i.e. supply oxygen and remove carbon dioxide. This is, however, not sufficient. Preferably, only air should be used (i.e. a low inspired oxygen concentration) and any damage on the cardiopulmonary system must be minimized. Oxygenation of blood is controlled by measuring partial pressure of oxygen ($P_aO_2$) instead of, for instance, saturation of oxygen ($S_aO_2$). $P_aO_2$ is preferred since it reflects gas exchange even at 100% $S_aO_2$. Further, pressures, in particular peak inspiratory pressure, PIP, and pressure amplitude of the inspiration pulse, should be as low as possible, since they will then cause the least physical harm to the lungs and the cardiovascular system. Since respiratory rate (RR) and inspiration/expiration time ratio (I:E ratio) can effect the pressure within the lungs at the end of expiration, so called intrinsic positive end expiratory pressure (intrinsic PEEP or $PEEP_i$), these are also varied in order to optimize them.

For most patients, PIP, PEEP (PIP−PEEP=pressure amplitude), RR and I:E ratio can be optimized by relatively simple means, thanks to the insights obtained by the invention. $P_aO_2$, blood pressure and expiration flow $\phi_E$ are the necessary measured parameters. The realization of the importance of and connection between these parameters has made real closed loop ventilation possible.

Returning to FIG. 4, in the first block 38 the entire procedure begins. In the second block 40, measurements of the partial pressure of oxygen $P_aO_2$ and the ventilatory condition, such as respiratory rate RR, are read by the control unit. A determination whether the lung is sufficiently open or not is then performed (block 42). This determination is in this case based on the measured $P_aO_2$. If the measured $P_aO_2$ is lower than a predetermined threshold value, the lungs are determined not to be open. If this is the case (output No in block 42), the opening protocol in block 44 is activated. In the opening protocol procedure, the lungs are opened and the oxygenation of the blood will thus improve. New settings may be required. Further measurement of $P_aO_2$ and reading of settings are then performed again in block 40, before a further test of the condition of the lung is made in block 46.

At this stage it is checked whether a closing pressure $P_c$ has been determined. If not (output No in block 46), the reduction protocol (block 48) will be activated. When the reduction protocol has been executed, the measurements and readings of block 40 are performed again. During the reduction protocol procedure it is determined whether new settings are preferable and whether there is hypoventilation or hyperventilation present.

When the closing pressure $P_c$ has been determined (output Yes in block 46), the maintenance and weaning protocol is activated in block 50. The maintenance and weaning protocol procedure is made to keep the lung open and, finally, wean the patient from the dependency of the artificial ventilation. In block 52, which follows the maintenance and weaning protocol, there is a test whether the weaning has been successful. If not (output No in block 52), the measurements and readings of block 40 are performed again. If the weaning has been successful (output Yes in block 52), the treatment is at an end (block 54), and the patient can be disconnected from the artificial ventilation system.

Referring now to FIGS. 5–17 a second method for obtaining an optimal ventilation of a patient's lung system is described.

The different protocols will also be described in more detail in connection with the second method.

Figure 5:
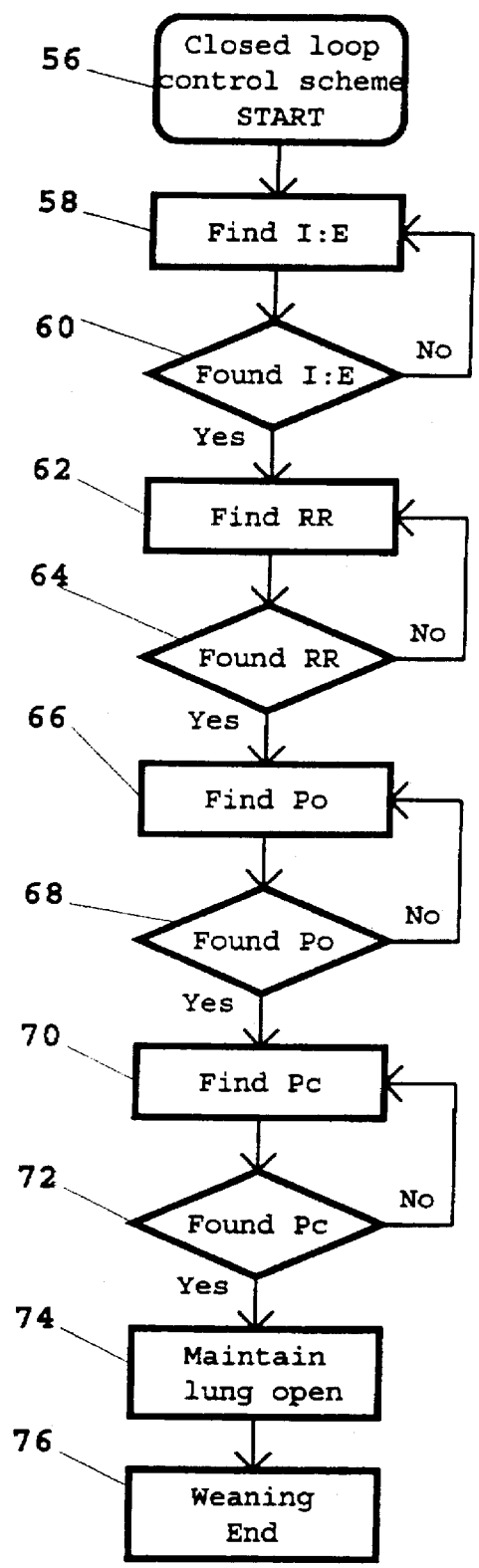
FIG. 5 is a flow chart illustrating a second embodiment of a method for controlling the ventilator system of FIG. 1, in accordance with the invention.

In FIG. 5 a flow chart illustrates the overall basis of the second method. The procedure begins with start block 56 and proceeds in block 58 with an attempt to find an optimal ratio between inspiration time and expiration time (I:E ratio). As long as it has not been found (output No in block 60), it will continue this procedure. When the optimum I:E ratio has been found (output Yes in block 60), an optimal respiratory rate (RR) is sought (block 62). As with the I:E ratio, the procedure of finding the optimal respiratory rate (RR) will continue as long as the optimal RR has not been found. When the optimal RR is determined (output Yes in block 64), the second method proceeds in block 66 by finding the opening pressure $P_o$. As with the previous determinations, a loop will continue between block 68 and block 66 until the opening pressure $P_o$ is found. Blocks 66 and 68 thus correspond to the opening protocol mentioned above. In some cases a "true" opening pressure $P_o$ will not be found (mainly due to very severe conditions of the lung). The second method then proceeds with the reduction protocol, which begins in block 70 by finding the closing pressure $P_c$. The closing pressure $P_c$ is basically the pressure at which the lungs will begin to collapse again, after having been opened up. In block 72, this test is performed until the closing pressure $P_c$ has been found. The found opening and closing pressures ($P_o$, $P_c$) are then set sequentially and the lungs are maintained open according to the maintenance protocol in block 74. The second method is concluded in block 76, with the weaning of the patient.

Figure 6:
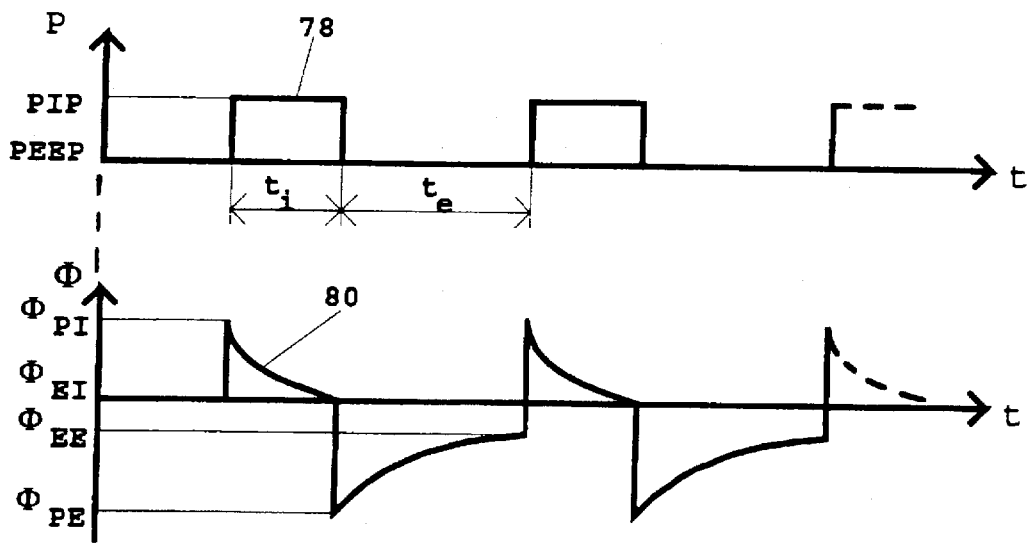
FIG. 6 shows a pressure diagram and a flow diagram for an inspiration pulse as used in the inventive method and apparatus.

In FIG. 6 two diagrams are shown. The first shows pressure in relation to time for an inspiration pulse 78. The inspiration pulse 78 has a low pressure on PEEP level and a peak pressure of PIP. The pulse 78 has an inspiration phase which lasts during the inspiration time $t_i$ and an expiration phase which lasts during the expiration time $t_e$. Below the pressure-time diagram, a flow-time diagram depicts the flow to and from the patient during inspiration and expiration. The flow curve 80 begins with a sharp increase up to a maximum inspiration flow $\phi_{PI}$ and an end inspiratory flow $\phi_{EI}$. The end inspiration flow $\phi_{EI}$ should always be zero (0). The tidal volumes will then have had time to be redistributed within the lung. During expiration, a high flow is established at first, the peak expiratory flow $\phi_{PE}$ since the pressure difference in the lungs and the ambient surroundings are high. At the end of the expiration, the end expiratory flow $\phi_{EE}$ is measured. The end expiratory flow, $\phi_{EE}$, is larger than zero if a new inspiration pulse commences before the pressure difference between gas in the lungs and the ambient surrounding (tubing) has been equalized. Based on the peak expiratory flow $\phi_{PE}$ and the end expiratory flow $\phi_{EE}$ a ratio of these can be calculated, i.e. the EEPk-flow. Based on the EEPk-flow, the optimum I:E ratio and optimum RR can be determined, as shown in the flow charts in FIGS. 7 and 8.

Figure 7:
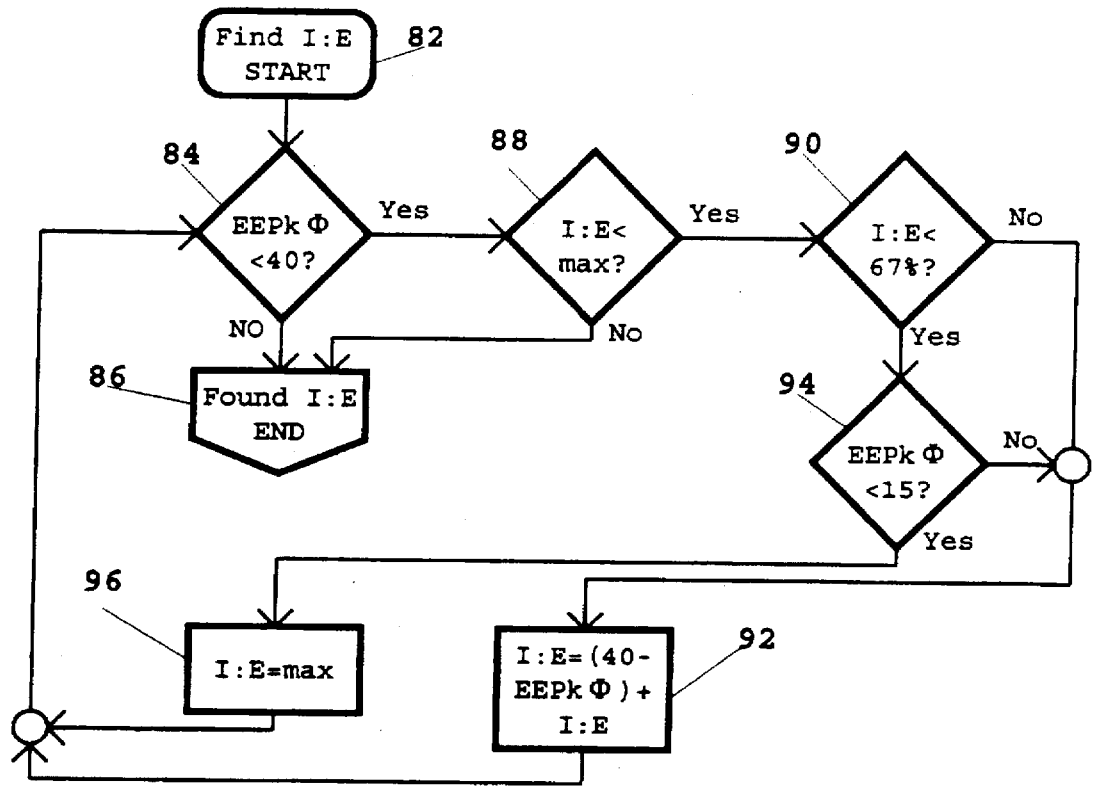
FIG. 7 is a flow chart showing a first series of steps in the second embodiment of the inventive method.

The substeps for finding the optimum I:E-ratio in the second method are described in FIG. 7, where the first block 82 is the start block. The mentioned EEPk-flow (EEPkφ) is then compared with a desired EEPkφ value, in this case 40. Since the end expiratory flow $\phi_{EE}$ is always smaller than the peak expiratory flow $\phi_{PE}$, the EEPkφ is always smaller than 1. The desired value 40 thus refers to the fraction, i.e. either 0.40 or 40%. The desired value, 40, used in this example, can be chosen from any value between 1 and 99, depending on the patient connected to the ventilation system (i.e. age, size or weight, sex, reason for need of artificial ventilation, etc.). The selection of a good value can be made based on the knowledge database. A preferable interval for the desired EEPkφ is, however, 30–40. The same is valid for I:E ratio, which usually is referred to as a percentage. If the EEPk-flow exceeds this desired EEPkφ value (output No in block 84), the optimum I:E ratio for the patient has been found, block 86. If the EEPk-flow is below 40 (output Yes in block 84), the I:E ratio is compared with a maximum setting for the I:E ratio, in block 88. Similar to the above, the value of the maximum I:E ratio depends on the patient and his/her status. Any percentage between 1 and 99% is possible. Again, the knowledge database would provide a preferable value for the individual patient. In this embodiment, the maximum I:E ratio is 80%. If the I:E ratio already is at the maximum (output No block 88), this I:E ratio is used as the optimal I:E ratio for the time being, since a better value can not be determined due to the patients condition. The sequence is then at an end (block 86).

If, however, the I:E ratio is below maximum (output Yes block 88), the I:E ratio is compared with a first I:E ratio threshold value, in this case 67%. If the I:E ratio exceeds 67% (output No block 90), a new I:E ratio is set in block 92, to be equal to the sum of 40 minus EEPk-flow and current I:E ratio. The procedure of determining and comparing the EEPk-flow with the desired EEPkφ value in block 84 is then repeated. If however the I:E ratio is below 67% (output Yes in block 90), the EEPk-flow is compared to a first EEPkφ threshold value in block 94. In this second comparison, the threshold value is 15. If the EEPk-flow exceeds 15 (output No block 94), a new I:E ratio is set according to block 92. If, however, the EEPk-flow is below 15 (output Yes block 94), the I:E ratio is set to the maximum value for the I:E ratio in block 96. The test is then resumed in block 84 by determining and comparing the current EEPk-flow with the first EEPkφ threshold value.

Figure 8:
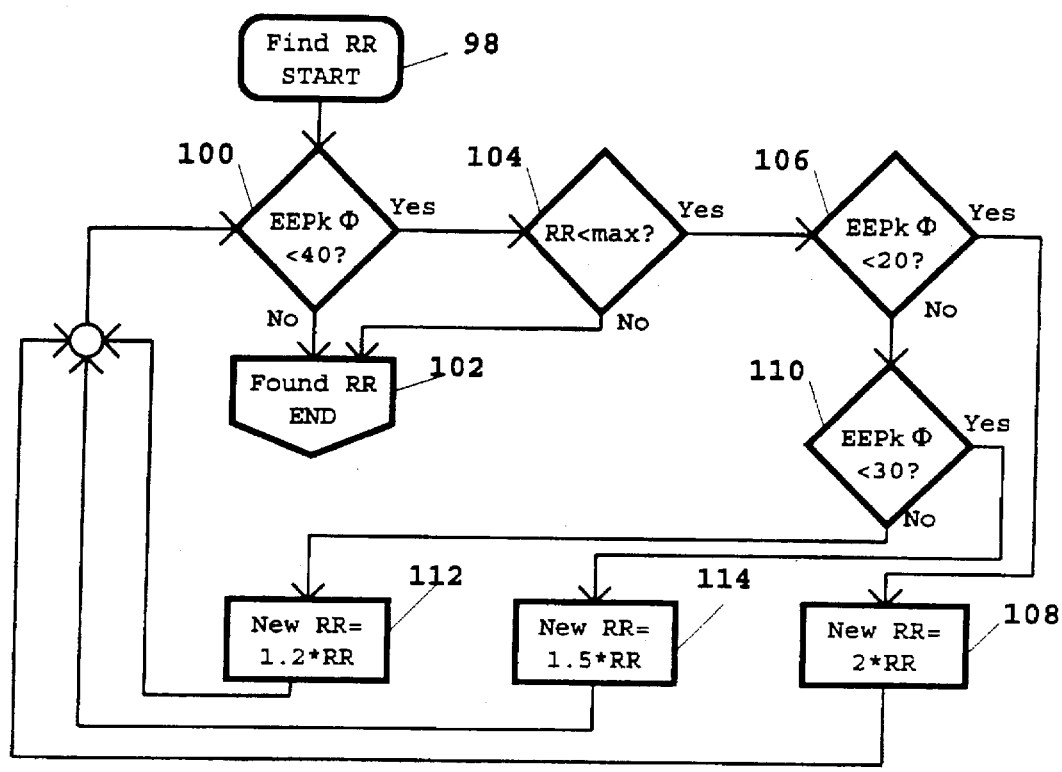
FIG. 8 is a flow chart showing a second series of steps for the second embodiment of the inventive method.

In a similar way, the flow chart in FIG. 8 illustrates the substeps required for finding the optimal respiratory rate RR. This procedure begins with start block 98 and, as in the evaluation of the optimal I:E ratio, the EEPk-flow is compared with a desired EEPkφ value, again 40, in block 100. If the EEPk-flow exceeds the desired EEPkφ value (output No), the optimal respiratory rate RR has been found and the procedure ends in block 102. If, however, the EEPk-flow is below the desired EEPkφ value (output Yes in block 100), the respiratory rate RR is compared to a maximum value for the respiratory rate RR in block 104. If the respiratory rate RR is already equal to the maximum value for the respiratory rate RR (output No), an optimum respiratory rate RR (for the time being) has been found and the procedure ends in block 102.

If the respiratory rate RR is below the maximum value for the respiratory rate (output Yes block 104), the EEPk-flow value is compared to a second EEPkφ threshold value in block 106. In this case the second EEPkφ threshold value is 20. If the EEPk-flow is above 20 (output Yes), a new respiratory rate RR is set to 2 times the current respiratory rate RR. If the EEPk-flow is above 20 (output No in block 106), the EEPk-flow is compared to a third EEPkφ threshold value, in this case 30, in block 110. If the EEPk-flow is above 30 (output No), a new respiratory rate RR is set to 1.2 times the current respiratory rate RR in block 112 and EEPk-flow is then determined and compared again with the first EEPkφ threshold value of 40 in block 100.

If the EEPk-flow does not exceed the third EEPkφ threshold of 30 (output Yes in block 110), a new respiratory rate RR is set to be equal to 1.5 times the respiratory rate in block 114 and the evaluation of EEPk-flow is resumed in block 100.

Figure 9:
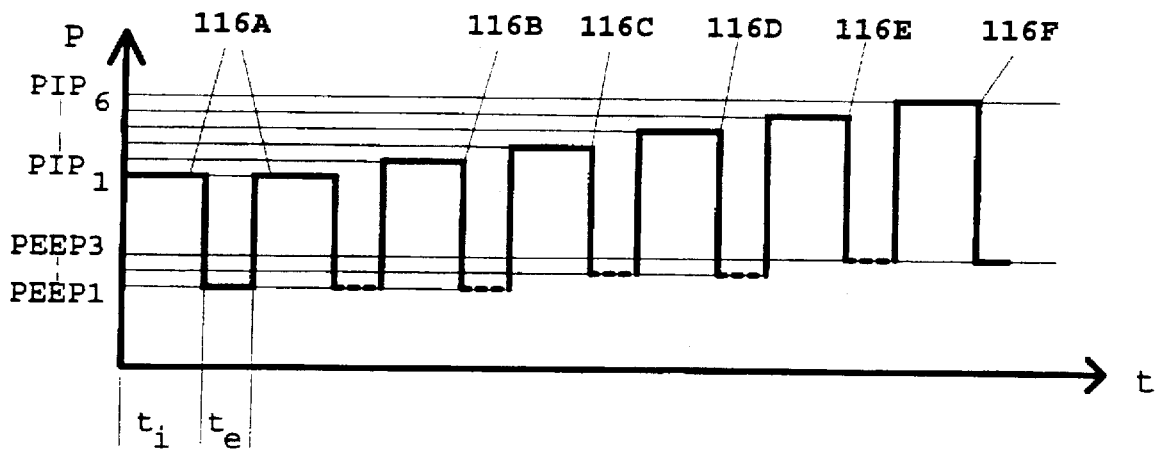
FIG. 9 illustrates a series of inspiration pulses for determining an opening pressure of a lung as used in the inventive method and apparatus.

These evaluation steps for I:E ratio and RR, as described in FIGS. 6 and 7, are then followed by the opening protocol. In FIG. 9 a series of inspiration pulses 116A–116F for determining an opening pressure $P_o$ is shown. The first two inspration pulses 116A have a positive end expiratory pressure of $PEEP_1$ and a peak inspiratory pressure of $PIP_1$. They have an inspiration time of $t_i$ and an expiration time of $t_e$. The inspiration and expiration times have been evaluated according to the schemes in FIG. 7 and 7 (both I:E ratio and RR effect $t_i$ and $t_e$). If the first inspiratory pulses 116A fails to open up the lungs sufficiently, as indicated by a sufficient $P_aO_2$, a new inspiration pulse or sequence of inspiration pulses 116B is utilized. The second inspiration pulse 116B has an elevated peak pressure $PIP_2$ but the same $PEEP_1$ as the first inspiration pulses 116A. In consecutive steps, the PIP and/or PEEP values will be increased as long as the lungs remain partially closed. The procedure continues either until the lungs open up sufficiently or until maximum settings are reached for PIP and PEEP levels.

Figure 10:
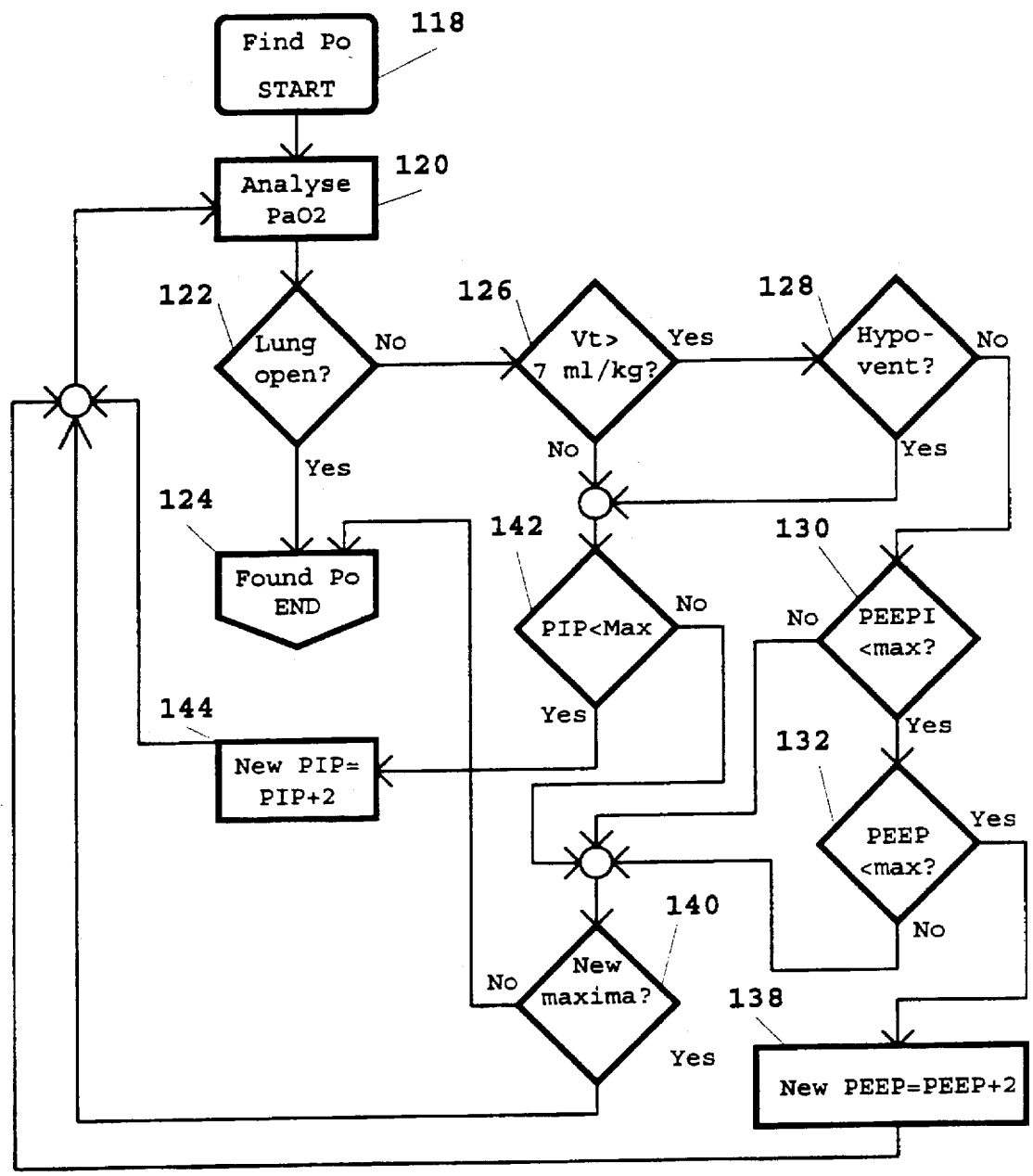
FIG. 10 is a flow chart showing a third series of steps in the second embodiment of the method of the invention.

The procedure for obtaining the opening pressure $P_o$ and determining the inspiration pulse sequence is described in the flow chart in FIG. 10 where start block 118 indicates the starting point for the opening protocol. The partial pressure of oxygen $P_aO_2$ is first analysed in block 120 (after delivery of a number of inspiration pulses) and the measured $P_aO_2$ is compared with a $P_aO_2$ threshold value for evaluating whether the lung is sufficiently open [or not]. When the lungs are sufficiently open (output Yes), the procedure has found the opening pressure $P_o$ and the sequence ends in block 124. If the lungs are not sufficiently open, the procedure will instead continue with block 126, where the tidal volume $V_t$ is compared with a $V_t$ threshold of 7 ml/kg. The exemplified threshold value (7 ml/kg) could also be selected from a wider range, 1–20 ml/kg, depending on the patient. Usually, values between 5 and 7 ml/kg are utilized. In other words, if the patient weighs 70 kg in this case the $V_t$ threshold is 490 ml. The patient's weight is entered on the control panel 10 or the monitor screen 16 as described in connection with FIG. 1. In the alternative, the monitoring unit 14 can be provided with a scales 14F for weighing the patient. Instead of weight, body size could be used for determining the tidal volume. The amount of fat on the patient will then not influence the tidal volume value (amount of fat is not correlated to the size of the lungs).

If the tidal volume $V_t$ is above the $V_t$ threshold (output Yes), hypoventilation is looked for in block 128. Hypoventilation means that the alveoli obtain an insufficient ventilation and the content of carbon dioxide $CO_2$ thus increases in the lungs and the blood system of the patient. If there is no hypoventilation (output No), the intrinsic PEEP is measured and compared with an allowed maximum intrinsic PEEP. If the intrinsic PEEP is below the maximum intrinsic PEEP value, output Yes, the external PEEP is compared with a maximum external PEEP value in block 132. If the external PEEP does not exceed the maximum external PEEP value (output No), a new PEEP is set equal to the current PEEP+2 $cmH_2O$, block 138. The procedure then resumes at block 120, the $P_aO_2$ analysis. Since it will take some time for the $P_aO_2$ to react on an increase in the gas exchange, due to an increase in the amount of opened up alveoli, one or a few minutes will have to pass before measurement is made.

If the external PEEP, however, is equal to or exceeds the maximum external PEEP value (output No in block 132) an evaluation whether new maxima should be allowed is made, in block 140. If a new maximum value for PEEP is to be allowed, the procedure resumes in block 120 with the new maximum PEEP value. Likewise, if the intrinsic PEEP is found to be above the maximum $PEEP_1$ value (output No in block 130), it is evaluated in block 140, for determining whether a new maximum value should be allowed.

Going back now to block 126, where the tidal volume $V_t$ was compared with a $V_t$ threshold of 7 ml/kg, if the tidal volume $V_t$ is lower than this the procedure continues with block 142 and compares the current PIP with a maximum PIP value. The maximum PIP value could be any value between 20 and 70 $cmH_2O$, but is preferably between 40 and 60 $cmH_2O$. If the current PIP is lower than the maximum PIP value (output Yes), a new PIP is set equal to previous PIP+2 $cmH_2O$ and the $P_aO_2$ analysis resumes in block 120. However, should PIP be above the maximum PIP value (output No), it will again be evaluated whether new maxima could be allowed in block 140. Otherwise the procedure is at an end (block 124), and the current PIP pressure is the opening pressure $P_o$. In such a case, the lungs cannot be opened without risking too much damage to the lungs. Finally, if hypoventilation is present (output Yes in block 128), the PIP is again compared with the maximum PIP value in block 142 and the procedure continues as described. Thereby an opening pressure $P_o$ or the maximum allowed pressure will have to be found for all lung systems.

It should be noted that the opening pressure may also be found according to any other known procedure for finding an opening pressure, in particular those described in earlier Swedish patent applications Nos. 9502031-9 and 9502032-7. Another way of obtaining an opening pressure is described in Swedish Published Application 501 560.

Figure 11:
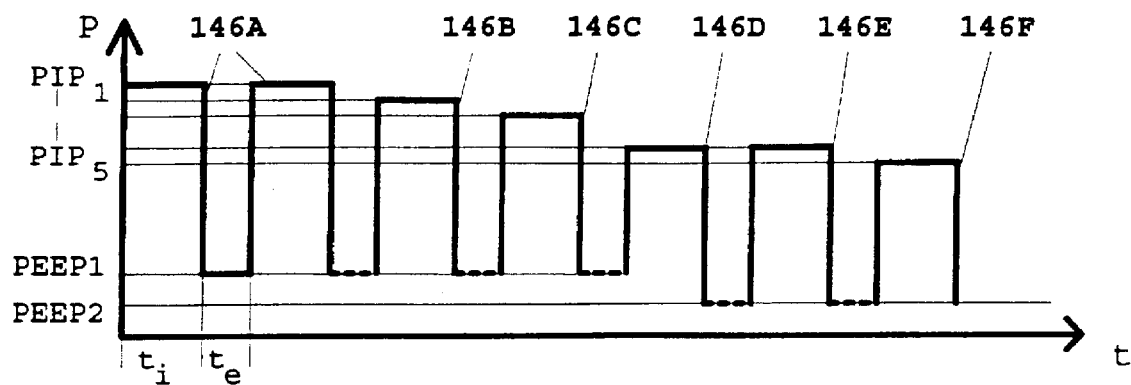
FIG. 11 illustrates a sequence of inspiration pulses for determining a closing pressure of a lung, as used in the inventive method and apparatus.

As the opening pressure has been found, the second method proceeds with the reduction protocol, which corresponds to blocks 70 and 72 in FIG. 5. The first phase of the reduction protocol is to determine at which pressure the lungs will collapse again, i.e. the closing pressure $P_c$. In FIG. 11, a series of inspiration pulses 146A–146E is shown. These inspiration pulses 146A–146E correspond to the inspiration pulse sequence shown in FIG. 9, but with reducing values for PIP and PEEP. Thus the second inspiration pulse 146B has a lower PIP than the first inspiration pulse 146A and the third inspiration pulse 146C has an even lower PIP. For the fourth inspiration pulse 146D, both the PEEP and the PIP have been reduced and for the fourth and fifth inspiration pulses 146E and 146F, small changes in the PIP are made. The procedure for finding the closing pressure $P_c$ is described in the flow chart in FIG. 12 and commences with the start block 148.

Similar to the steps for finding the opening pressure $P_o$, the $P_aO_2$ is analysed in block 150 and thereafter a check is made whether the lung is open or not in block 152. In all further references to measuring of $P_aO_2$, it is assumed that any changes in the condition of the alveoli has had time to influence the $P_aO_2$. When the lungs are open no longer, the closing pressure $P_c$ has been determined and the procedure for finding the closing pressure will be ended in block 154. However, this will normally not be the case in the beginning of the procedure and the lungs would normally be open (output Yes block 152). It is then checked whether severe hypoventilation is present in block 156. If there is severe hypoventilation (output Yes), it is checked whether external PEEP exceeds a minimum external PEEP value in block 162. If external PEEP is lower than the minimum external PEEP value (output No), it is checked whether a new minima should be allowed in block 160. If not, the procedure ends in block 154. If a new minimum value is allowed (output Yes), the procedure resumes with the analysis of $P_aO_2$ in block 150. If external PEEP is higher than the minimum external PEEP value (output Yes), a new PEEP is set equal to the current PEEP −2 $cmH_2O$ in block 164 and the procedure resumes with the analyse of the $P_aO_2$ in block 150.

If the check for severe hypoventilation in block 156 results in a negative answer (output No), it is checked whether PIP exceeds the minimum PIP value in block 166. If the PIP is lower than the minimum PIP value (output No), the procedure continues by checking for hyperventilation, block 158. Hyperventilation is caused by unnecessary high ventilation of the alveoli and is indicated by a low carbon dioxide production. This can be measured either in the expired respiratory gas or by analysing the partial pressure of carbon dioxide $P_aCO_2$ in the blood. If there is hyperventilation (output Yes), it will be necessary to check whether new minimum values should be allowed in block 160. Returning now to block 158 and the control for hyperventilation. If there is no hyperventilation (output No), PEEP is evaluated as described above in block 162.

However, if PIP is still above minimum (output Yes in block 166), the procedure continues in block 168 by checking whether the tidal volume $V_t$ is lower than 7 ml/kg (similar to the check in connection with FIG. 10). If the tidal volume $V_t$ is indeed lower than this $V_t$ threshold value (output Yes), the procedure continues by checking whether there is hypoventilation in block 170 and if so (output Yes), it will resume with block 162.

If any of the checks in blocks 168 and 170 has a negative result, that is, if the tidal volume $V_t$ is above 7 ml/kg or if there is no hypoventilation, the current PIP is compared to a first PIP threshold value in block 172. In this case, the first PIP threshold value is 40 $cmH_2O$. If PIP is above the first PIP threshold value, which could very well be the case in the beginning of the closing pressure ($P_c$) procedure, a new PIP is set equal to the current PIP minus a first predefined decrement, e.g. 3 $cmH_2O$ in block 174. After the new PIP has been set, the $P_aO_2$ is again analyzed in block 150. Again, there should be a certain time lapse before the analylis is carried out to assure that any reactions in the lungs and blood system due to the lowered PIP have time to take place. If the current PIP is already below 40 $cmH_2O$ (output No in block 172), the current PIP is compared with a second PIP threshold value in block 176. The second PIP threshold value is in this case 25 $cmH_2O$ and if the current PIP exceeds this second PIP threshold value (output Yes), a new PIP is set to be equal to the current PIP minus a second predefined decrement, e.g. 2 $cmH_2O$ in block 178. As before, when a new value has been set the $P_aO_2$ is analyzed in block 150. Should PIP be below even 25 $cmH_2O$, it will be is compared with a third PIP threshold value in block 180. The third PIP threshold is the programmed minimum PIP value, which could be e.g. 20 $cmH_2O$. Since PIP is normally a measured PIP value, it might at this stage be below the minimum PIP value, although it was above the minimum value in the control made in block 166. Should this occur, the procedure would resume at block 158, as was the case when the PIP was below the minimum PIP value in block 166. Normally, however, at this stage of the procedure, the current PIP will at least be above the minimum value, output Yes, and a new PIP is set to be equal to the current PIP minus a third predefined decrement, e.g. 1 cmH$_2$O, block 182. The procedure then resumes by analysing the P$_a$O$_2$ in block 150. This procedure, with subsequent lowering of the PIP and PEEP values, continues until the lungs are considered to have collapsed again. In other words, when the measured P$_a$O$_2$ falls below a predetermined P$_a$O$_2$ threshold value, or displays a significant change between two P$_a$O$_2$ measurements which is above a certain defined level, the procedure will end.

It should be noted that changes in the blood gas parameter (P$_a$O$_2$) can also be used for determining new settings. For example, when determining opening and closing pressures, the change in measured P$_a$O$_2$ could be used for determining a new PIP or PEEP.

When the closing pressure PC has been found, the next phase, the steps of maintaining the lung open, can follow. This is shown in the flow chart in FIG. 13. The start is indicated in block 184 and the first thing to do is to set the determined opening and closing pressures (P$_o$ and P$_c$) sequentially, block 186. Since this procedure has the major task of maintaining the lungs open, this is checked in blocks 187 and 188 by analyzing P$_a$O$_2$ and comparing it with the threshold value. Should it at any time be discovered that the lungs are not open, as reflected in the measured P$_a$O$_2$, a new opening pressure P$_o$ and closing pressure P$_c$ must be found, i.e. the procedures described in the flow charts of FIGS. 9 and 11 would be repeated in order to find these two important pressure values. As long as the lung remains open (output Yes), the maintenance procedure continues by checking for hyperventilation in block 192. If there is no hyperventilation present (output No), it is instead checked whether hypoventilation is present in block 194. As long as there is no hypoventilation (output No), the haemodynamics are checked in block 195. These controls, for hyperventilation in block 192, for hypoventilation in block 194 and for the haemodynamics in block 195, are all important parts in the main structure of the invention of ventilating the patient with the lowest pressures possible without impeding on the lung system or the blood system. If the haemodynamics are also OK (output Yes in block 195), the procedure is at an end in block 196. This procedure will then be repeated at predetermined intervals during the treatment of the patient in order to make sure that the patient status is still stable.

Should there be hyperventilation present (output Yes in block 192), it has to be evaluated whether this depends on the respiratory rate, the PEEP pressure, the PIP, or if the dead space can be increased. This evaluation procedure is shown in a flow chart in FIG. 14.

This evaluation starts in block 206 and the first thing to do is to increase the respiratory rate by a factor of 1.2, block 208. Hyperventilation is then checked for in block 210, and if the increase in the respiratory rate was successful there will no longer be hyperventilation and the evaluation ends in block 212. If hyperventilation is still present (output Yes), it is checked whether the respiratory rate RR has already been increased twice in block 214. If not, respiratory rate is again increased by a factor of 1.2 in block 208 and hyperventilation is checked for again. If the respiratory rate RR has been increased twice (output Yes in block 214), then the respiratory rate will not be further increased. Instead, it is checked whether PEEP is greater than the maximum PEEP value in block 216. If PEEP is lower than the maximum PEEP value, PEEP will be increased by 2 CmH$_2$O in block 218. It is then checked whether the increase in PEEP has had an effect on the hyperventilation in block 220. If there is no hyperventilation any longer, the evaluation ends in block 212, with the new settings for respiratory rate RR and PEEP. If, however, hyperventilation is still present, PEEP will be increased in steps of 2 cmH$_2$O until it reaches the maximum PEEP value. If, during this time, hyperventilation has not ceased, the PIP will have to be decreased instead in block 222. PIP is decreased by 1 cmH$_2$O. After this decrease it is first checked whether the lungs are still open in block 224. If they are, it is checked whether the increase in PIP has been able to stop the hyperventilation in block 226. If there is no hyperventilation present, the evaluation has been successful and ends in block 212. If there is still hyperventilation, the dead space of the ventilation system is increased in block 228. Dead space is then increased until there is no hyperventilation present. After each increase in dead space, it is also checked whether the lungs are still sufficiently open in block 224. Should the measured P$_a$O$_2$ indicate that the lungs are not open any longer, they will have to be opened up again, block 230, and the maintenance procedure will then have to resume again in block 232. It should be noted that block 232 (maintain the lung open), in FIG. 14 corresponds to the maintain lung open procedure described in FIG. 13.

If the dead space has to be increased, there are several ways of solving this. The immediate solution is of course to physically increase the dead space, especially by adding more tubing between the patient and the artificial ventilation system. However, this requires that the patient be disconnected from the artificial ventilation system and if he/she has not recovered sufficiently, this could cause the lungs to collapse. When the new tubing have been added, the entire procedure may thus have to be repeated by starting the evaluation scheme from the beginning. This is the main reason why it is checked whether the lungs are still open after each increase in dead space.

Figure 16:
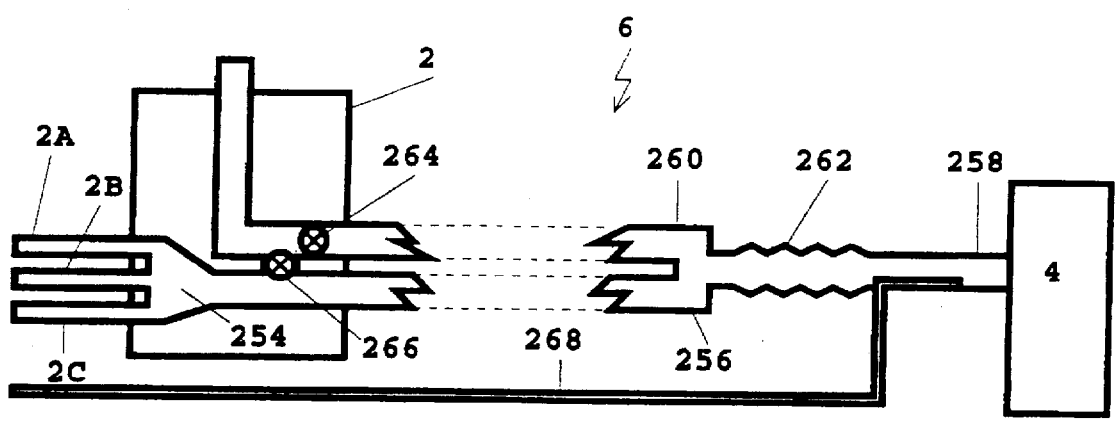
FIG. 16 illustrates a respiratory gas delivery system, which can be used as an artificial ventilation system in accordance with the principles of the present invention.

FIG. 16 shows a connecting system 6 for the artificial ventilation system. The connecting system 6 connects the respiratory gas driving unit 2 and the patient 4 to each other. The connecting system has a mixing chamber 254 in which the gases from respective gas inlets 2A, 2B, 2C are mixed into the respiratory gas. The mixed respiratory gas is supplied via a inspiration tube 256 to a tracheal tube 258 or a corresponding connection tube to the patient. Expired respiratory gas flows from the patient via the tracheal tube 258 and an expiration tube 260. On the tracheal tube 258 a section 262 consisting of a expandable-compressible material could be placed for changing the dead space without disconnecting the patient. By expanding the section 262, the dead space will increase.

Another way of expanding the dead space is achieved by the use of a first valve 264 and a second valve 266. The first valve is located within the expiration tube 260 and may control the flow in the expiration tube 260. The second valve 266 is located in a connection between the inspiration tube and the expiration tube within the gas delivery unit 2. The second valve 266 is normally closed and the respiratory gas passes through the connection system 6 as described. However, by opening the second valve 266 and closing the first valve 264 during the last part of the expiration, expired gas will not be able to flow in the expiration tube 260, since this has been sealed off by the first valve 264. Instead the expired gas will flow into the inspiration tube 256 in the direction towards the opening between the inspiration tube 256 and expiration tube 260, i.e. the second valve 266. A part of the inspiration tube 256 will then act as an extension of the tracheal tube 258, or operate as an expansion of the section 262. As the next inspiration pulse is delivered the first valve 264 will open and the second valve 266 will close and the inspiration will commence as any other normal inspiration.

A further gas connection 268 is also included in the system. The further gas connection is connected to a controllable gas source and ends in the tracheal tube 258. The flow of gas within the further gas tube 268 can be controlled simultaneously with the respiratory gas flow, so that the total amount of gas supplied to the patient is controlled at a high degree. The further gas tube 268 could be used in a yet further way of increasing dead space, or rather, to obtain a similar effect. Instead of physically changing dead space, a small content of carbon dioxide could be added to the respiratory gas either directly through one of the gas inlets 2A 2B, 2C or via the further gas tube 268. This addition of carbon dioxide could be operated so it supplies a small amount of carbon dioxide at the onset of inspiration, whereby it would simulate an increased dead space. The amount of added carbon dioxide could be calculated for each individual patient by comparing either with values measured when there was no hyperventilation or with the body weight or with other calculations.

Figure 13:
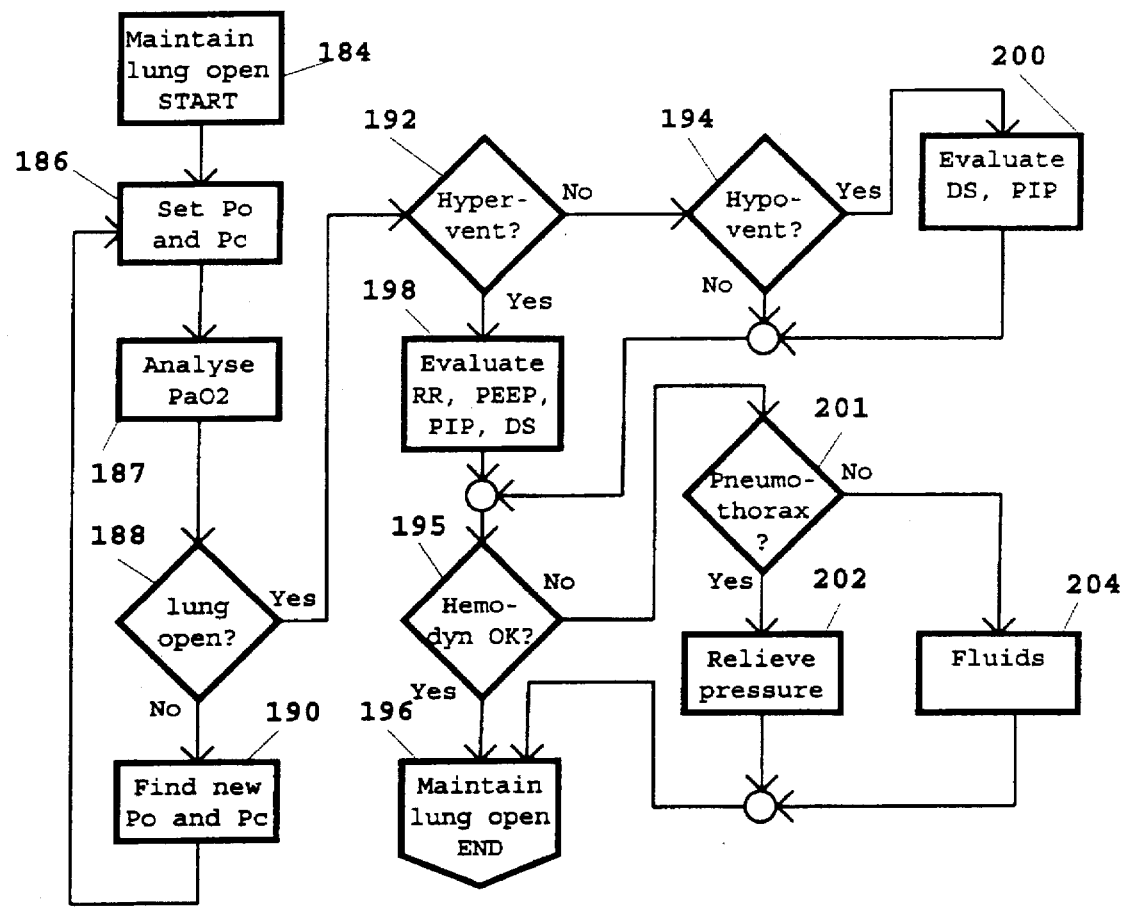
FIG. 13 is a flow chart showing a fifth series of steps for the second embodiment of the inventive method.
Figure 12:
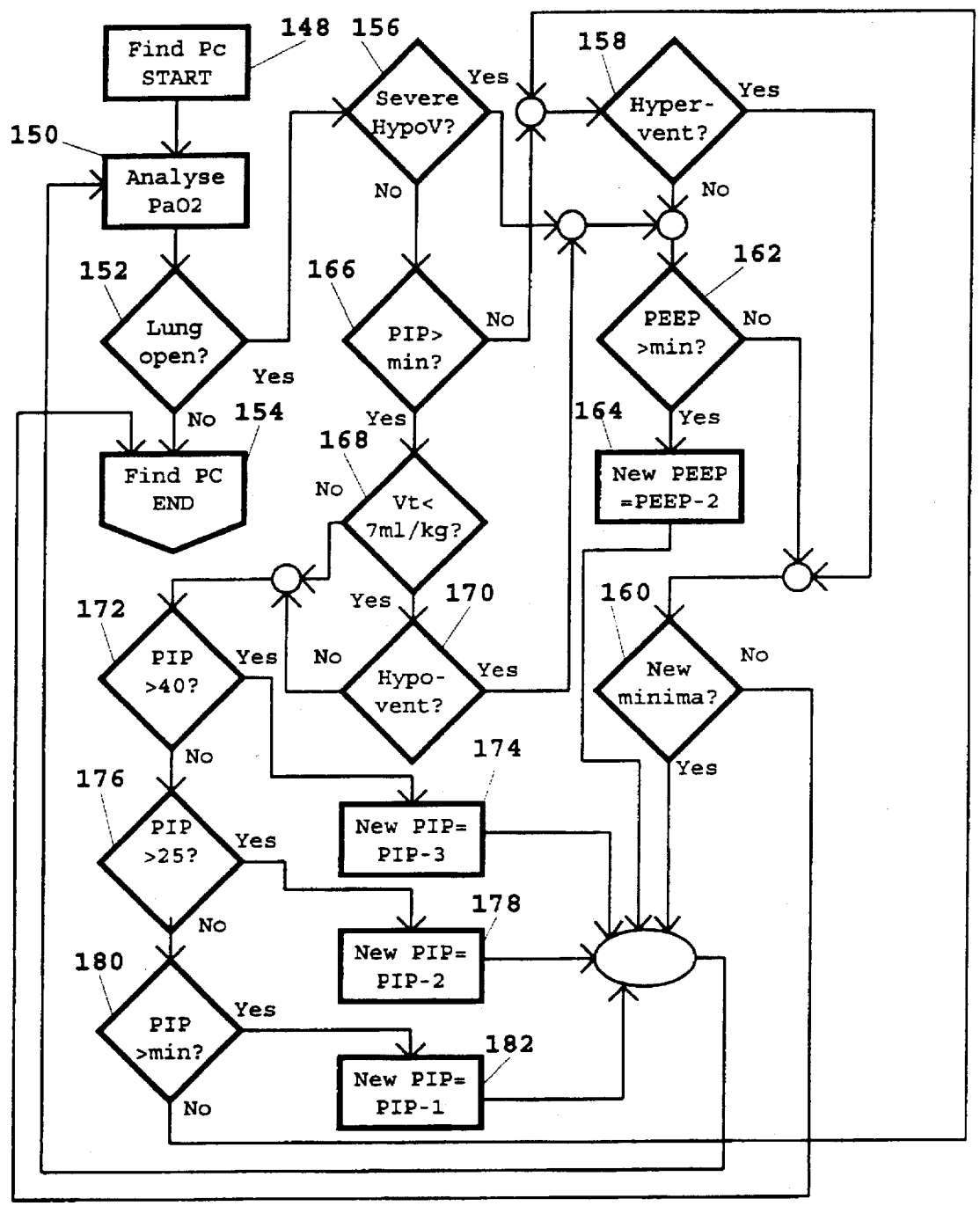
FIG. 12 is a flow chart showing a fourth series of steps for the second embodiment of the inventive method.
Figure 14:
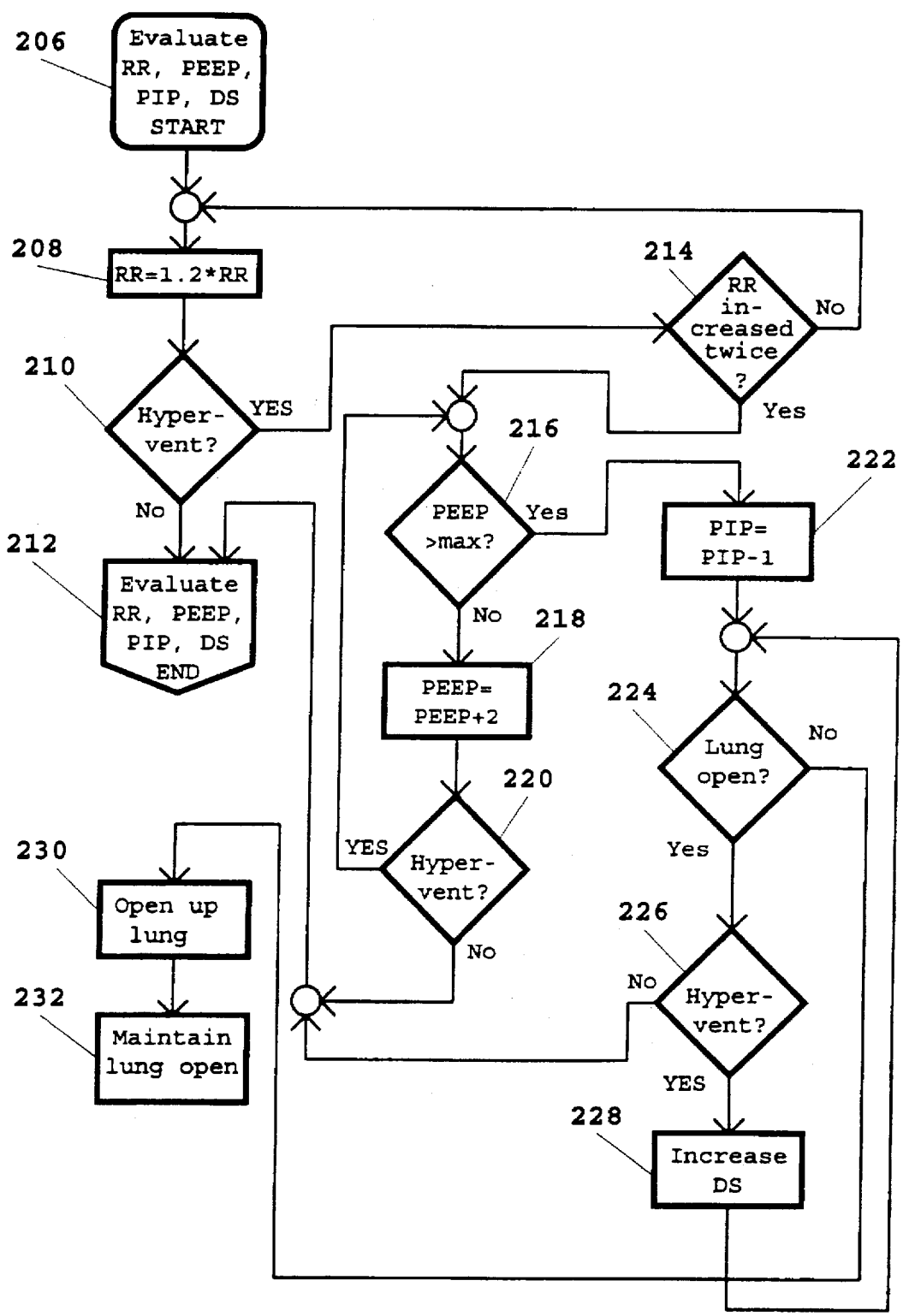
FIG. 14 is a flow chart showing a sixth series of steps for the second embodiment of the inventive method.

When all the checks, resulting from the detection of hyperventilation, have been made and evaluations have resulted in a new setting of any kind, the maintenance procedure in FIG. 13 resumes.

Figure 15:
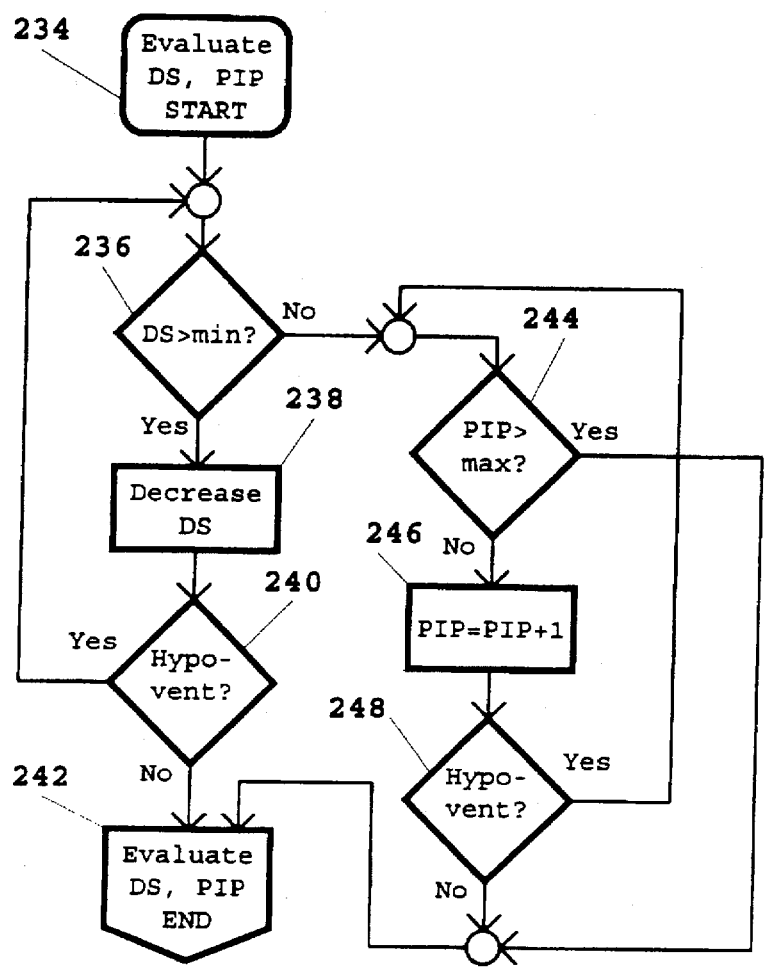
FIG. 15 is a flow chart showing a seventh series of steps for the second embodiment of the inventive method.

Referring again to FIG. 13, should there instead be hypoventilation present (output Yes in block 194), there is an evaluation made in block 200 whether the dead space is too large or whether there is a wrong peak inspiratory pressure PIP. This evaluation is shown in FIG. 15, which commences with the start block 234. First, it is checked whether the dead space exceeds the minimum value of the dead space, block 236. If the dead space exceeds the minimum value, the dead space is decreased in block 238. Thereafter it is again checked whether there is hypoventilation in block 240. If not the evaluation is over (block 242). As long as there is hypoventilation and the dead space exceeds the minimum value, this sequence is repeated. If there is still hypoventilation when the dead space reaches the minimum value of the dead space (output No in block 236), it is checked whether the current PIP exceeds the maximum PIP allowed, block 244. If the current PIP does not exceed the maximum PIP, the current PIP value is increased by 1 cmH$_2$O in block 246. As for the evaluation described for hyperventilation situations, PIP is then increased by 1 cmH$_2$O until hypoventilation ceases, or the maximum PIP is reached. Again, the maximum PIP ensures that damaging pressures are avoided. Thus, hypoventilation is looked for in block 248. If the hypoventilation has ceased before the current PIP has reached the maximum PIP, the evaluation is at an end in block 242. If, however, hypoventilation persists (output Yes in block 246), and the current PIP has reached the maximum PIP, then hypoventilation has to be accepted for the time being and the evaluation comes to an end in block 242.

In similarity to the hyperventilation condition the dead space could easily be changed by physically removing some of the tubing which causes the hypoventilation to occur in the patient. Again this would mean that the entire procedure may have to be repeated, since there is a risk that the patient's lungs may collapse during the disconnection of the patient. Referring again to FIG. 16, the patient does not necessarily have to be disconnected. The expandable section 262 could be compressed in order to decrease the dead space. Another way of decreasing the dead space is to provide air at the end of the expiration phase via the further gas tube 268. Hereby the last expired volume will be mixed with a defined amount of air and as the inspiration phase commences the rebreathed amount of respiratory gas will be lower. If the dead space has been increased by utilizing the above described function (FIG. 16) of the first valve 264 and the second valve 266, the dead space may easily be decreased by going back to a normal inspiration/expiration timing, i.e. not utilizing this function of the first valve 264 and second valve 266.

If the check for hemodynamics in block 195 in FIG. 13 should indicate that there is hemodynamic depression, it will be necessary to check if there is a pneumothorax, i.e. if air has entered the pleural space in the lungs in block 201. Pneumothorax is in many cases caused by a penetration of the chest wall. In open pneumothorax the lung will collapse and not contribute to the ventilation. During artificial ventilation there is, however, a higher probability that there will be a closed pneumothorax. The closed pneumothorax is a rupture in the lung, causing a direct connection between the bronchial system and the pleural space. If there is a pneumothorax present (output Yes), the pressure must be relieved, block 202, e.g. by inserting a chest tube. The haemodynamics are preferably controlled by checking for cardiovascular depression based on the blood pressure measurements made by the monitoring unit. Other known measurements indication haemodynamic depression can, of course, also be used.

If there is cardiovascular depression but no pneumothorax (output No in block 201), or if a pneumothorax has been relieved at an earlier stage, an intravascular fluid test should be given, in block 204. If the fluid test is successful more fluids should be given up to an allowed maximum volume. Thereafter cardiovascular active drugs should be given to the patient in order to overcome these distresses and negative side-effects for the patient. When all these measures have been taken, which a physician could indicate by queuing a certain code on the control panel or on the monitor screen in the artificial ventilator system, the maintenance sequence is at an end in block 196.

At predetermined time intervals the control unit will execute the maintenance procedure.

When the patient has improved sufficiently, it is time for weaning him/her. The basic principle when weaning a patient is not to force the patient to breathe spontaneously immediately. Slowly at first, and then, when the patient takes a sufficient amount of spontaneous breaths, a more rapid transition from the controlled ventilation to support modes of ventilation.

Figure 17:
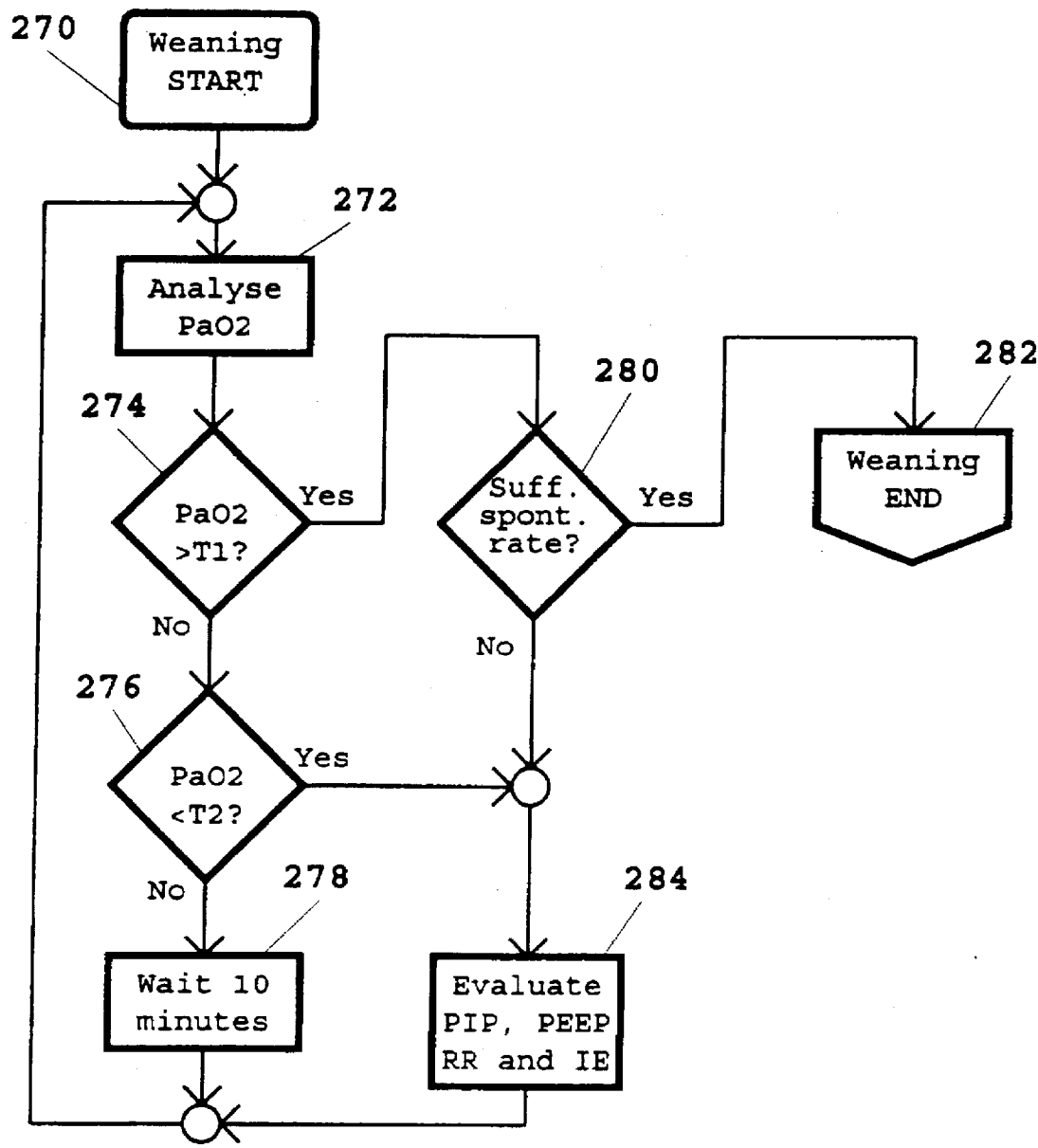
FIG. 17 is a flow chart showing an eighth series of steps for the second embodiment of the inventive method.

In FIG. 17 this is described by a flow chart. The weaning protocol, or procedure, commences in block 270. As for the preceding protocols, the P$_a$O$_2$ is measured, in block 272. The measured P$_a$O$_2$ is then compared with a first threshold T1, in block 274. The first threshold Ti corresponds to a level of good oxygenation. It should be remembered that at this stage in the treatment of a patient, the lungs are open and the patient practically recovered from the condition which required the artificial ventilation.

Should the measured P$_a$O$_2$ be lower than the first threshold T1 (output No), it is compared with a second threshold T2, in block 276. The second threshold T2 corresponds to a level of oxygenation which is considered sufficient. If the measured P$_a$O$_2$ is equal to or exceeds the second threshold T2, i.e. falls between the first threshold Ti and the second threshold T2, the current settings are maintained for the time being, and a new measurement of P$_a$O$_2$ is performed after a predetermined time lapse, in this case 10 minutes, block 278, and the procedure resumes with block 272.

Should the measured $P_aO_2$ be equal to or exceed the first threshold T1 in block 274, the patients spontaneous respiration rate ($RR_s$) is measured and compared with a $RR_s$, threshold, block 280. The RRs threshold correlates to a sufficient spontaneous breathing, and if the measured spontaneous rate exceeds this threshold, output Yes, the weaning is at an end (block 282).

However, should the measured spontaneous respiratory rate be insufficient, or if the measured $P_aO_2$ is lower than the second threshold T2, an evaluation of the settings is made, in block 284, before the procedure resumes again in block 272—with new settings. Depending on whether the measured $P_aO_2$ was too low or the measured spontaneous respiratory rate was too low, the current settings of PIP, PEEP, RR and I:E ratio can be increased or decreased.

It should be noted that the figures used in the description for threshold values, as well as for minima and maxima, are given only as examples. These figures could be different depending on, inter alia, the species treated (human or animal), age (neonatal, infant, child, adult) and kind of illness. In the most straightforward realisation of the artificial ventilation system according to the invention, it could be adapted to automatically treat at least 90–99% of all adults, and require overriding settings from a physician in the remaining cases (before they too can be treated automatically).

Although modifications and changes may be suggested by those skilled in the art, it is the intention of the inventors to embody within the patent warranted hereon all changes and modifications as reasonably and properly come within the scope of their contribution to the art.

We claim as our invention:

1. In an artificial ventilation system having a respiratory gas delivery unit, connectable to a lung system of a living being for automatically generating and delivering controllable inspiration pulses of respiratory gas to the lung system, a regulating unit connected to the respiratory gas delivery unit for controlling the generation and delivery of inspiration pulses based on a control signal supplied to the regulating unit, a monitoring unit for measuring at least one parameter related to the function of the lung system and a control unit connected to the monitoring unit for determining a change in an inspiration pulse parameter, the improvement of the monitoring unit, control unit and regulating unit forming a closed loop, and monitoring unit comprising a blood gas analyzer connected to the blood system of the living being for measuring a blood gas parameter, and the control unit comprising means for determining an optimal peak inspiratory pressure and pressure amplitude for the controllable inspiration pulse based on the measured blood gas parameter for providing a sufficient oxygenation of the blood system and for minimizing negative cardiopulmonary influence including at least one of barotrauma, volutrauma, overdistension and hypoxic vasoconstriction, and for generating said control signal for causing said regulating unit to generate and deliver inspiration pulses having said optimal peak inspiratory pressure and pressure amplitude.

2. The improvement of claim 1, wherein the blood gas analyzer comprises means for measuring the partial pressure of oxygen $P_aO_2$ in the blood system wherein and the control unit comprises means for determining a minimum peak inspiratory pressure and pressure amplitude, for which the measured $P_aO_2$ exceeds a predetermined $P_aO_2$ threshold value.

3. The improvement of claim 2, wherein the monitoring unit further comprises a flow meter for measuring a flow of respiratory gas relative to the lung system and wherein the control unit comprises means for determining at least one parameter of the inspiration pulse selected from the group consisting of external positive end expiratory pressure, respiration rate and inspiration/expiration time ratio.

4. The improvement of claim 3, wherein the control unit comprises means for determining an end expiratory flow and a peak expiratory flow and an optimal respiration rate based on a quotient between the determined end expiratory flow and peak expiratory flow.

5. The improvement of claim 1 further comprising a monitor screen connected to the monitoring unit for displaying measured parameters.

6. The improvement of claim 1 wherein control unit comprises means for generating the control signal based on the determined change in the inspiration pulse parameter.

7. The improvement of claim 1 further comprising a manually operable control panel connected to the regulating unit for providing a further control signal based on a manually entry and said control panel comprising means for determining whether the control signal or the further control signal has precedence.

8. The improvement of claim 1 wherein the control unit comprising means for determining an opening pressure of the lung system.

9. The improvement of claim 8, wherein that the control unit comprises a means for determining a closing pressure of the lung system.

10. The improvement of claim 1 wherein the blood characterized in that the blood gas analyser comprises means for measuring the partial pressure of carbon dioxide ($P_aCO_2$) in the blood system.

11. The improvement of claim 1 wherein the monitoring unit comprises a $CO_2$— meter for measuring the $CO_2$ content of expired respiratory gas and the control unit comprises means for determining at least one $CO_2$— parameter selected from the group consisting of end tidal, $CO_2$ $CO_2$ minute production, $CO_2$ tidal production, ineffective tidal volume, effective tidal volume and effective ventilation.

12. The improvement of claim 10 wherein the control unit comprises means for determining, at predetermined intervals, whether hypoventilation is present.

13. The improvement of claim 12 wherein the control unit comprises means, when hypoventilation is present, for determining a change in at least one of the peak inspiratory pressure and the dead space of the artificial ventilation system for removing the hypoventilation condition.

14. The improvement of claim 10 wherein the control unit comprises means for determining, at predetermined intervals, whether hyperventilation is present.

15. The improvement of claim 14 wherein the control unit comprises means, when hyperventilation is present, for determining a change in at least one parameter selected from the group consisting of peak inspiratory pressure, the positive end expiratory pressure, the dead space of the artificial ventilation system and the respiratory rate, for removing the hyperventilation condition.

16. The improvement of claim 1 wherein the monitoring unit comprises a blood pressure meter for measuring a blood pressure of the blood system and wherein the control unit comprises means for determining at predetermined intervals, whether cardiovascular depression is present, and if cardiovascular depression is present, for generating a cardiovascular depression signal comprising a humanly perceptible alarm signal.

17. The improvement of claim 1 wherein the control unit comprises means for determining a new inspiration pulse parameter by iteratively changing a current inspiration pulse parameter and monitoring an effect on at least one measured parameter after a predetermined number of inspiration pulses, having the new inspiration pulse parameter, have been delivered to the lung system.

18. Method for automatically controlling an artificial ventilation system, connectable to the lung system of a living subject, comprising the steps of:

a) determining an optimal ratio between inspiration time and expiration time by comparing a measured ratio of a measured end expiratory flow and a measured peak expiratory flow to a reference ratio of end expiratory flow to peak expiratory flow;

b) determining an optimal respiration rate also by comparing said measured ratio to said reference ratio;

c) measuring blood gas parameter of the living subject and determining an opening pressure ($PO_2$) of the lung system from said blood gas parameter;

d) determining a closing pressure of the lung system at which the lungs will collapse;

e) at intervals, monitoring the condition of the lung including making an updated measurement of said blood gas parameter and, if necessary determining a change in an inspiration pulse delivered to the lung system system dependent on at least one of steps (a) through (d); and f) ordering a change in the inspiration pulse for provoking spontaneous respiration.

19. Method according to claim 18, wherein step a) comprises the following substeps:

a1) reading a current I:E ratio;

a2) measuring an end expiratory flow ($\phi_{EE}$);

a3) measuring a peak expiratory flow ($\phi PE$);

a4) calculating a EEPk$\phi$-ratio between the measured end expiratory flow ($\phi_{EE}$) and the peak expiratory flow ($\phi_{PE}$);

a5) comparing the calculated EEPk$\phi$-ratio with a predetermined first EEPk$\phi$-threshold value;

a6) if the calculated EEPk$\phi$-ratio exceeds the first EEPk$\phi$-threshold value, determining the current I:E ratio as the optimal I:E ratio;

a7) if the calculated EEPk$\phi$-ratio does not exceed the first EEPk$\phi$-threshold value, comparing the current I:E ratio with a predetermined maximum I:E ratio;

a8) if the current I:E ratio exceeds the predetermined maximum I:E ratio, determining the current I:E ratio as the optimum I:E ratio;

a9) if the current I:E ratio does not exceed the predetermined maximum I:E ratio, comparing the current I:E ratio with a predetermined I:E ratio threshold;

a10) if the current I:E ratio exceeds the predetermined I:E ratio threshold, calculating a new I:E ratio, which is equal to the difference between the first EEPk$\phi$-threshold value minus the calculated EEP$\phi$-ratio and the current I:E ratio and repeating the procedure from sub-step a1);

a11) if the current I:E ratio does not exceed the predetermined I:E ratio threshold, comparing the calculated EEPk$\phi$-ratio with a second EEPk$\phi$-threshold value;

a12) if the calculated EEPk$\phi$-threshold value, setting a new I:E ratio to be equal to the maximum I:E ratio and repeating the procedure from sub-step a1); and a13) if the calculated EEPk$\phi$-ratio does not exceed the second EEPk$\phi$-threshold value, determining the current I:E ratio as the optimum I:E ratio.

20. Method according to claim 19, wherein the first EEPk$\phi$-threshold value is between 30 and 40, the second EEPk$\phi$-threshold value is between 10 and 20 and the I:E ratio threshold is between 60 and 80%.

21. Method according to claim 18, wherein step b) comprises the following substeps:

b1) reading a current respiration rate;

b2) measuring an end expiratory flow ($\phi_{EE}$);

b3) measuring a peak expiratory flow ($\phi_{PE}$);

b4) calculating a EEPk$\phi$-ratio between the measured end expiratory flow ($\phi_{EE}$) and the peak expiratory flow ($\phi_{PE}$);

b5) comparing the calculated EEPk$\phi$-ratio with a predetermined first EEPk$\phi$-threshold value;

b6) if the calculated EEPk$\phi$-ratio exceeds the first EEPK$\phi$-threshold value, determining the current respiration rate as the optimal respiration rate;

b7) if the calculated EEPk$\phi$-ratio does not exceed the first EEPk$\phi$-threshold value, comparing the current respiration rate with a predetermined maximum respiration rate;

b8) if the current respiration rate exceeds the predetermined maximum respiration rate, determining the current respiration rate as the optimum respiration rate;

b9) if the current respiration rate does not exceed the predetermined maximum respiration rate, comparing the calculated EEPk$\phi$-ratio with a second EEPk$\phi$-threshold value;

b10) if the calculated EEPk$\phi$-ratio exceeds the second EEPk$\phi$-threshold value, comparing the calculated EEPk$\phi$-ratio with a third EEPk$\phi$-threshold value;

b11) if the calculated EEPk$\phi$-ratio exceeds the third EEPk$\phi$-threshold value, determining a new respiration rate to be equal to the current respiration rate multiplied by a first factor and repeating the procedure from sub-step b1);

b12) if the calculated EEPk$\phi$-ratio does not exceed the third EEPk$\phi$-threshold value, determining a new respiration rate to be equal to the current respiration rate multiplied by a second factor and repeating the procedure from sub-step b1); and b13) if the calculated EEPk$\phi$-ratio does not exceed the second EEPk$\phi$-threshold value, determining a new respiration rate to be equal to the current respiration rate multiplied by a third factor and repeating the procedure from sub-step b1).

22. Method according to claim 21, wherein the first EEPk$\phi$-threshold value is 40, the second EEPk$\phi$-threshold value is 20, the third EEPk$\phi$-threshold value is 30, the first factor is 1.2, the second factor is 1.5 and the third factor is 2.

23. Method according to claim 18, wherein step c) comprises the following substeps:

c1) obtaining the lean body weight of the living being;

c2) delivering a predetermined number of inspiration pulses having a current peak inspiratory pressure (PIP) and a current positive end expiratory pressure (PEEP);

c3) measuring the partial pressure of oxygen ($P_aO_2$) in a blood system of the living being;

c4) comparing the measured $P_aO_2$ with a predetermined $P_aO_2$ threshold value;

c5) if the measured $P_aO_2$ exceeds the predetermined $P_aO_2$ threshold value, determining the PIP as the opening pressure ($P_o$) and storing the determined opening pressure ($P_o$) and current PEEP;

c6) if the measured $P_aO_2$ does not exceed the predetermined $P_aO_2$ threshold value, measuring an inspiration flow ($\phi$) to the living being, determining a tidal volume ($V_t$) of supplied respiratory gas, calculating a quotient between the determined tidal volume ($V_t$) and the lean body weight and comparing calculated quotient with a predetermined $V_t$ threshold value;

c7) if the calculated quotient exceeds the predetermined $V_t$ threshold value, measuring a carbon dioxide content ($CO_2$ content) and comparing the measured $CO_2$ content with a predetermined $CO_2$ content threshold value;

c8) if the calculated quotient does not exceed the predetermined $V_t$ threshold value or if the measured $CO_2$ content exceeds the predetermined $C_2O$ content threshold value, comparing the current PIP with a predetermined maximum PIP value;

c9) if the current PIP does not exceed the maximum PIP value, setting a new current PIP to be equal to the current PIP plus a first predetermined increment and repeating the procedure from substep c2);

c10) if the measured $CO_2$ content does not exceed the predetermined $C_2O$ content threshold value, measuring the intrinsic positive end expiratory pressure ($PEEP_i$) and comparing it with a predetermined maximum $PEEP_i$ value;

c11) if the measured $PEEP_i$ does not exceed the predetermined maximum $PEEP_i$ value, comparing the current PIP with the maximum PIP value;

c12) if the current PIP does not exceed the predetermined maximum PIP value, setting a new current PIP to be equal to the current PIP plus a second predetermined increment, setting a new current PEEP to be equal to the current PEEP plus a third predetermined increment and repeating the procedure from substep c2);

c13) if the current PIP exceeds the predetermined maximum PIP value, comparing the current PEEP with a predetermined maximum PEEP value;

c14) if the current PEEP does not exceed the predetermined maximum PEEP value, setting a new current PEEP to be equal to the current PEEP plus a fourth predetermined increment and repeating the procedure from substep c2);

c15) if the current PEEP exceeds the predetermined maximum PEEP value, or if the $PEEP_i$ in substep c10) exceeds the predetermined maximum $PEEP_i$ value, or if the current PIP in substep c8) exceeds the predetermined maximum PIP value, determining whether a new maximum PIP value, a new maximum $PEEP_e$ value or a new maximum $PEEP_i$ value should be allowed;

c16) if new maxima are not allowed, determining the current PIP as the opening pressure ($P_o$) and storing the determined opening pressure ($P_o$) and current PEEP; and c16) if new maxima are allowed, setting these and repeating the procedure from substep c2).

24. Method according to claim 23, wherein the predetermined $V_t$ threshold value is between 5 and 7 ml/kg, the first predetermined increment is 2 $cmH_2O$, the second predetermined increment is 2 $cmH_2O$, the third predetermined increment is 2 $cmH_2O$ and the fourth predetermined increment is 2 $cmH_2O$.

25. Method according to claim 18, wherein step d) comprises the following substeps:

d1) delivering a predetermined number of inspiration pulses having a current peak inspiratory pressure (PIP) and a current positive end expiratory pressure (PEEP);

d2) measuring pressure in or near the lung system, respiratory gas flow, partial pressure of oxygen in the blood system and a $CO_2$ content, either in expired air or in the blood system;

d3) comparing the measured $P_aO_2$ with a predetermined $P_aO_2$ threshold value;

d4) if the measured $P_aO_2$ does not exceed the predetermined $P_aO_2$ threshold value, determining the current PIP as the closing pressure $P_c$ and storing the determined closing pressure $P_c$ and current PEEP;

d5) if the measured $P_aO_2$ does not exceed the $P_aO_2$ threshold value, comparing the $CO_2$ content is compared with a first predetermined $CO_2$ content threshold value;

d6) if the $CO_2$ content exceeds the first predetermined $CO_2$ content threshold value, comparing the current PIP with a predetermined minimum PIP value;

d7) if the current PIP exceeds the predetermined minimum PIP value, determining the tidal volume ($V_t$) and comparing it with a predetermined $V_t$ threshold value;

d8) if the determined tidal volume ($V_t$) does not exceed the predetermined $V_t$ threshold value, comparing the $CO_2$ content with a second predetermined $CO_2$ content threshold value;

d9) if the determined tidal volume ($V_t$) exceeds the predetermined $V_t$ threshold value or if the $CO_2$ content does not exceed the second predetermined $CO_2$ threshold value, comparing the current PIP with a first PIP threshold value;

d10) if the current PIP exceeds the first PIP threshold value setting a new current PIP to be equal to the current PIP minus a first predetermined decrement and repeating the procedure from substep d1);

d11) if the current PIP does not exceed the first PIP threshold value, comparing the current PIP with a second PIP threshold value;

d12) if the current PIP exceeds the second predetermined PIP threshold value, setting a new current PIP to be equal to the current PIP minus a second predetermined decrement and repeating the procedure from substep d1);

d13) if the current PIP does not exceed the second predetermined PIP threshold value, comparing the current PIP with a predetermined minimum PIP value;

d14) if the current PIP exceeds the predetermined minimum PIP value, setting a new current PIP to be equal to the current PIP minus a third predetermined decrement and repeating the procedure from substep d1);

d15) if the current PIP does not exceed the predetermined minimum PIP value, or if the $CO_2$ content in substep d5) exceeds the first predetermined $CO_2$ threshold value, or if the current PIP in substep d6) does not exceed the predetermined minimum PIP value, or if the $CO_2$ content exceeds the second predetermined $CO_2$ threshold value, comparing the $CO_2$ content with a third threshold value;

d16) if the $CO_2$ content exceeds the third $CO_2$ threshold value, comparing the current PEEP with a predetermined minimum PEEP value;

d17) if the current PEEP exceeds the predetermined minimum PEEP value, setting a new current PEEP to be equal to the current PEEP minus a fourth decrement and repeating the procedure from substep d1);

d18) if the current PEEP does not exceed the predetermined minimum PEEP value or if the $CO_2$ content does not exceed the third $CO_2$ content threshold value, determining whether a new minimum PIP value, or a new minimum PEEP value can be allowed;

d19) if new minimum values are allowed, setting the new minimum values and repeating the procedure from substep d1); and d20) if new minimum values are not allowed, determining the current PIP as the closing pressure $P_c$ and storing the determined closing pressure $P_c$ and current PEEP.

26. Method according to claim 25, wherein the predetermined $V_t$ threshold value is between 5 and 7 ml/kg, the first predetermined PIP threshold value is between 30 and 45 $cmH_2O$, the second predetermined PIP threshold value is between 20 and 30 $cmH_2O$, the first predetermined decrement is 3 $cm_2HO$, the second predetermined decrement is 2 $cmH_2O$, the third predetermined decrement is 1 $cmH_2O$ and the fourth predetermined decrement is 2 $cmH_2O$.

27. Method according to claim 18, wherein step e) comprises the following substeps:

e1) measuring pressure, $CO_2$ content, $P_aO_2$ and blood pressure;

e2) comparing measured $P_aO_2$ with a predetermined $P_aO_2$ threshold;

e3) if the measured $P_aO_2$ does not exceed the predetermined $P_aO_2$ threshold value, repeating steps c) and d);

e4) if the measured $P_aO_2$ exceeds the $P_aO_2$ threshold, comparing the $C_2O$ content with a first predetermined $CO_2$ threshold value;

e5) if the $CO_2$ content exceeds the first predetermined $CO_2$ threshold value, altering the settings for respiratory rate (RR), positive end expiratory pressure (PEEP), peak inspiratory pressure (PIP) and/or dead space (DS) until the measured $CO_2$ content no longer exceeds the first predetermined $CO_2$ threshold value;

e6) if the $CO_2$ content does not exceed the first predetermined $CO_2$ threshold value, comparing the $CO_2$ content with a second predetermined $C_2O$ threshold value;

e7) if the $CO_2$ content exceeds the second predetermined $CO_2$ threshold value, altering the settings of dead space (DS) and/or peak inspiratory pressure (PIP) until the $CO_2$ content does not exceed the second predetermined $CO_2$ threshold value or until maximum/minimum values for dead space and PIP are reached;

e8) if the $CO_2$ content does not exceed the second predetermined $CO_2$ threshold value, comparing the blood pressure with a predetermined blood pressure interval;

e9) if the measured blood pressure falls within the predetermined blood pressure interval, ending step e); and e10) if the blood pressure falls outside the predetermined blood pressure interval, generating an alarm.

* * * * *